(12) United States Patent
Steinbach et al.

(10) Patent No.: US 7,060,013 B2
(45) Date of Patent: Jun. 13, 2006

(54) VERSATILE HEALTH CARE APPARATUS

(75) Inventors: John M. Steinbach, Charlotte, NC (US); Kevin F. Bulson, Charlotte, NC (US); Elbert D. Turner, III, Charlotte, NC (US)

(73) Assignee: Bedside Rehabilitation Technology, Inc., Charlotte, NC (US)

( * ) Notice: Subject to any disclaimer, the term of this patent is extended or adjusted under 35 U.S.C. 154(b) by 410 days.

(21) Appl. No.: 10/183,474

(22) Filed: Jun. 28, 2002

(65) Prior Publication Data

US 2004/0002410 A1     Jan. 1, 2004

(51) Int. Cl.
    *A63B 21/045*    (2006.01)
(52) U.S. Cl. .................................... 482/127; 482/904
(58) Field of Classification Search ........ 482/121–130, 482/10, 72, 904; 602/32–36
    See application file for complete search history.

(56) References Cited

U.S. PATENT DOCUMENTS

| | | | | |
|---|---|---|---|---|
| 1,867,642 A | * | 7/1932 | Woods | 482/125 |
| 3,826,490 A | | 7/1974 | Mossman | |
| 3,885,789 A | * | 5/1975 | Deluty et al. | 482/120 |
| 4,523,620 A | | 6/1985 | Mortellite | |
| 5,005,829 A | | 4/1991 | Caruso | |
| 5,226,867 A | * | 7/1993 | Beal | 482/127 |
| 5,242,347 A | * | 9/1993 | Keeton | 482/102 |
| 5,370,594 A | * | 12/1994 | Grinblat | 482/72 |
| 5,505,681 A | * | 4/1996 | Bruggemann | 482/127 |
| 5,582,850 A | | 12/1996 | Cloeren et al. | |
| 5,733,231 A | * | 3/1998 | Corn et al. | 482/120 |
| 5,820,519 A | * | 10/1998 | Slenker | 482/4 |
| 6,149,559 A | * | 11/2000 | Mackey | 482/124 |
| 6,228,004 B1 | | 5/2001 | Steinbach et al. | |
| 6,413,196 B1 | * | 7/2002 | Crowson | 482/118 |
| 6,659,922 B1 | * | 12/2003 | Yu | 482/127 |
| 6,811,541 B1 | * | 11/2004 | Lambert | 602/36 |

FOREIGN PATENT DOCUMENTS

GB                755763         8/1956

OTHER PUBLICATIONS

Orthopedic Systems, Inc., *The Versitrack Cervical Traction System*.

* cited by examiner

*Primary Examiner*—Jerome Donnelly
*Assistant Examiner*—Fenn C. Mathew
(74) *Attorney, Agent, or Firm*—Timothy R. Kroboth

(57) ABSTRACT

A versatile health care apparatus that can be used for physical therapy, or to exert a desired pulling force on a patient's body and maintain the pulling force, is disclosed. Beneficially, in a first aspect, the apparatus includes a power spring, a pull-line connected to the power spring, and mounting apparatus for securing the apparatus to varied support structures. Beneficially, this apparatus further includes when used for physical therapy, a pair of ergonomically spaced apart guide wheels.

In accordance with a second aspect of the invention, the apparatus includes a pull-line, and a rotatable pull-line wheel mounted on an axle and operatively connected to a power spring in connection with the axle, and the pull-line has an end in connection with the pull-line wheel. In accordance with this aspect of the invention, the exercise load for physical therapy may advantageously be increased or a desired pulling force may be exerted on a patient's body, by rotating the axle in an appropriate direction so that energy is applied to the power spring, and an axle rotation-preventing element of the apparatus is thereafter engaged to maintain the increased load or to maintain the pulling force.

25 Claims, 13 Drawing Sheets

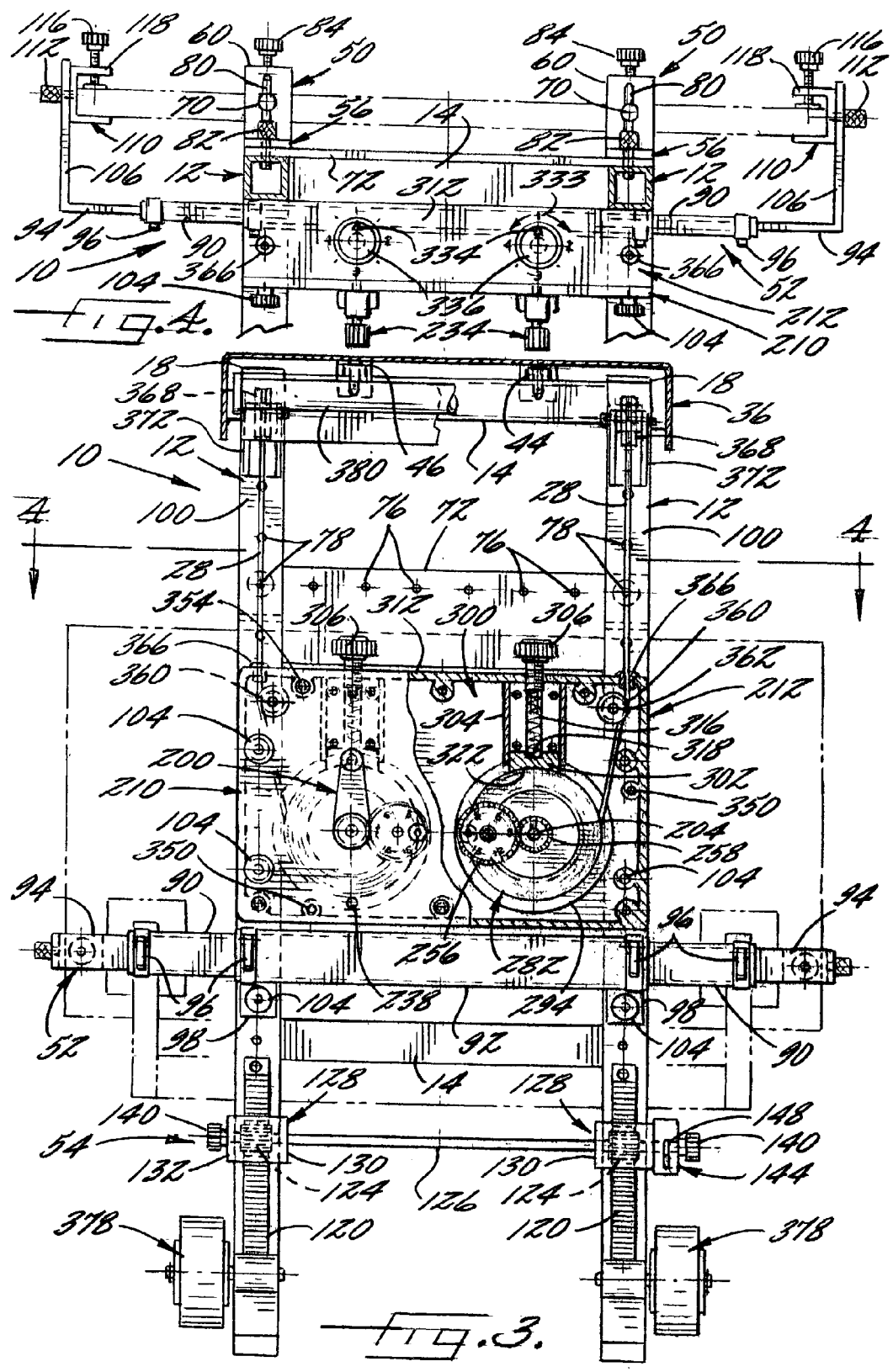

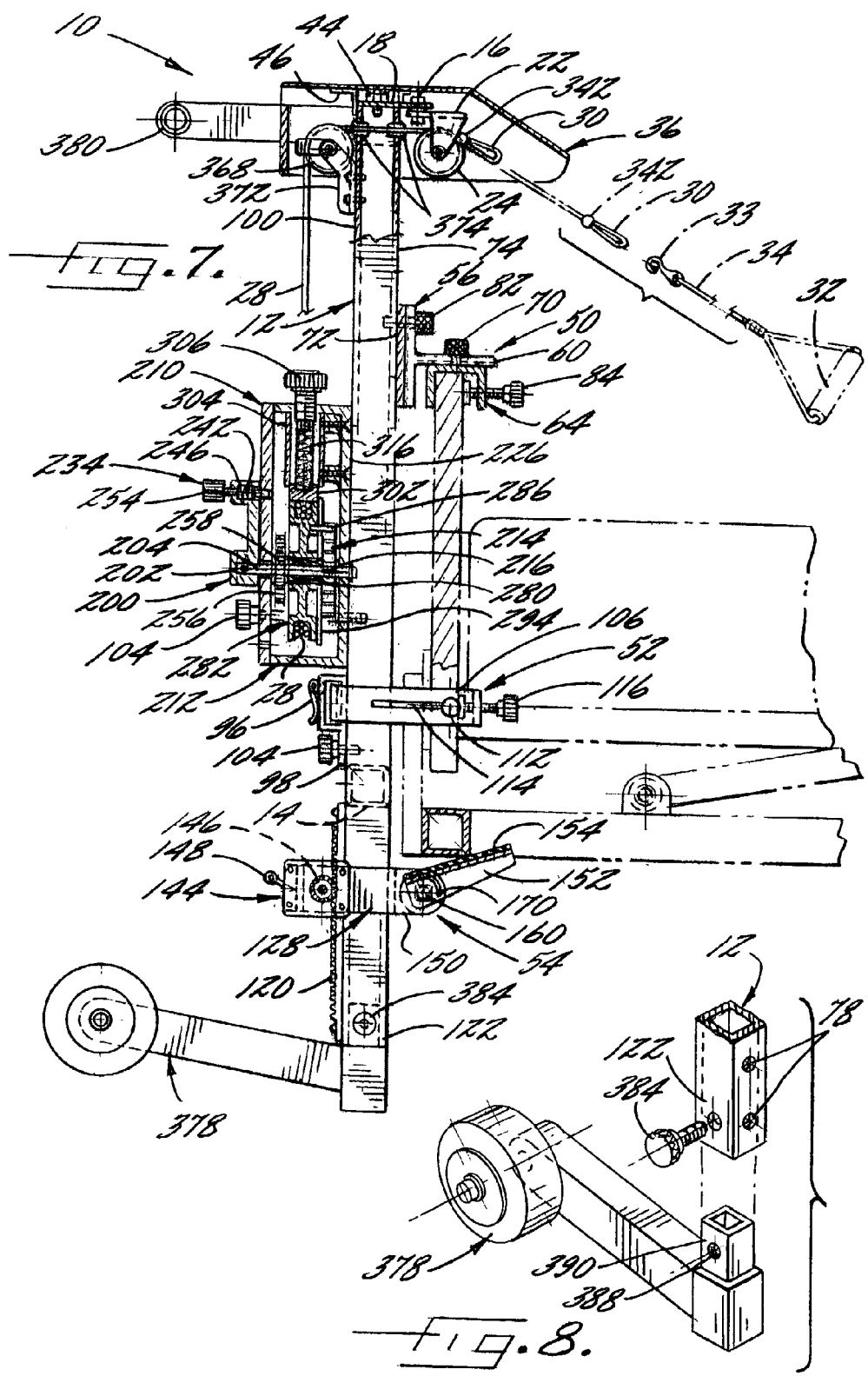

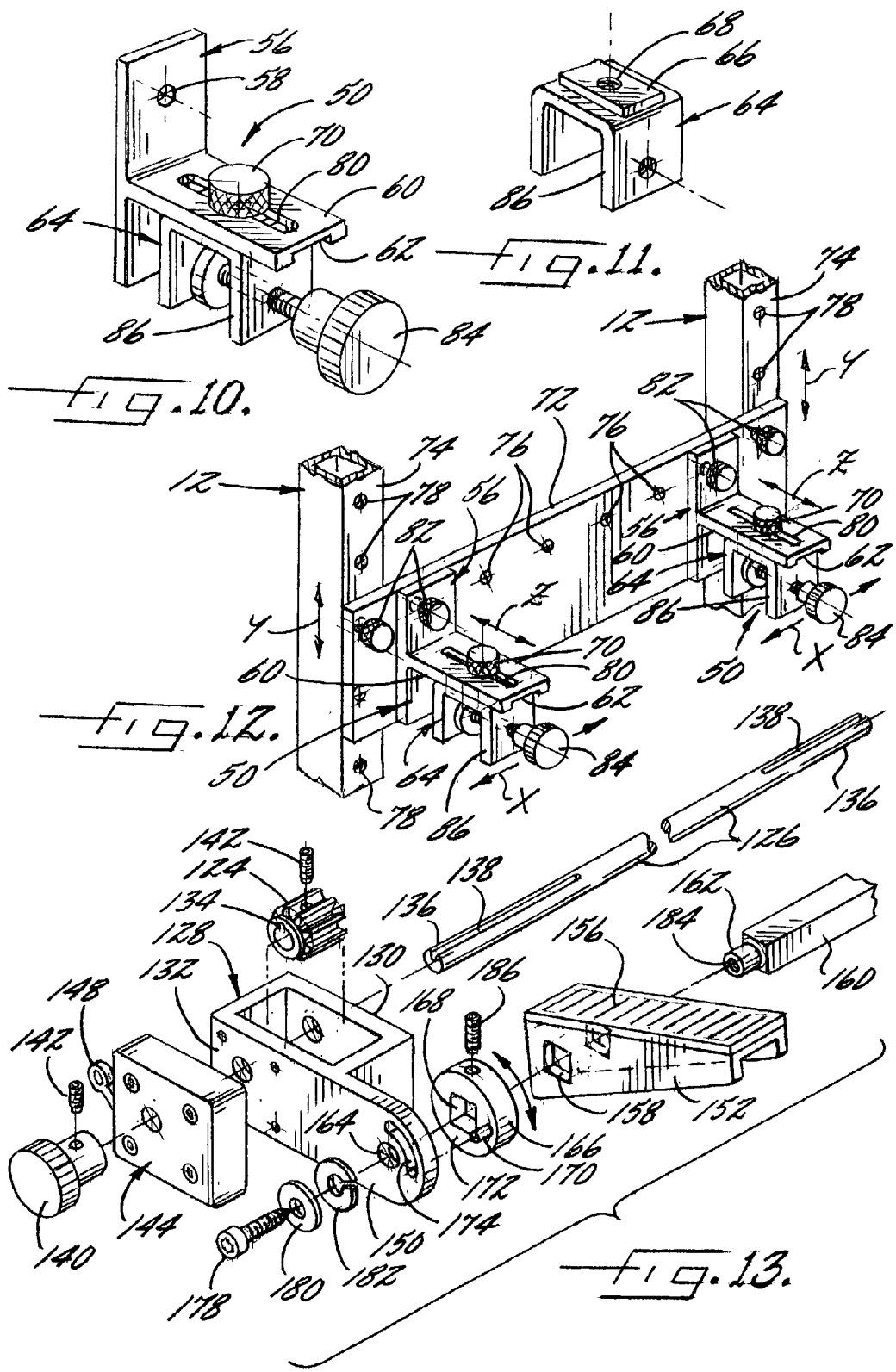

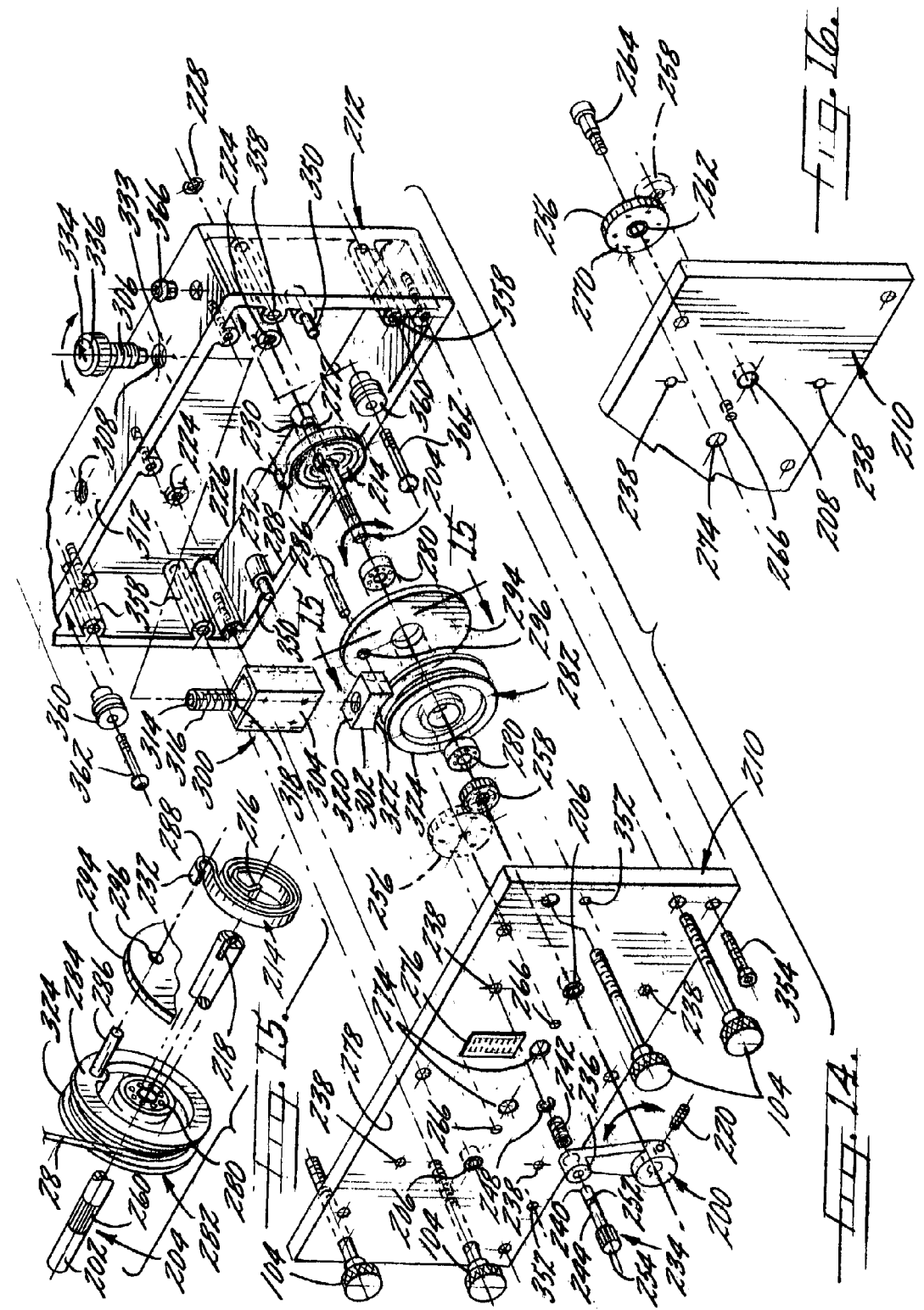

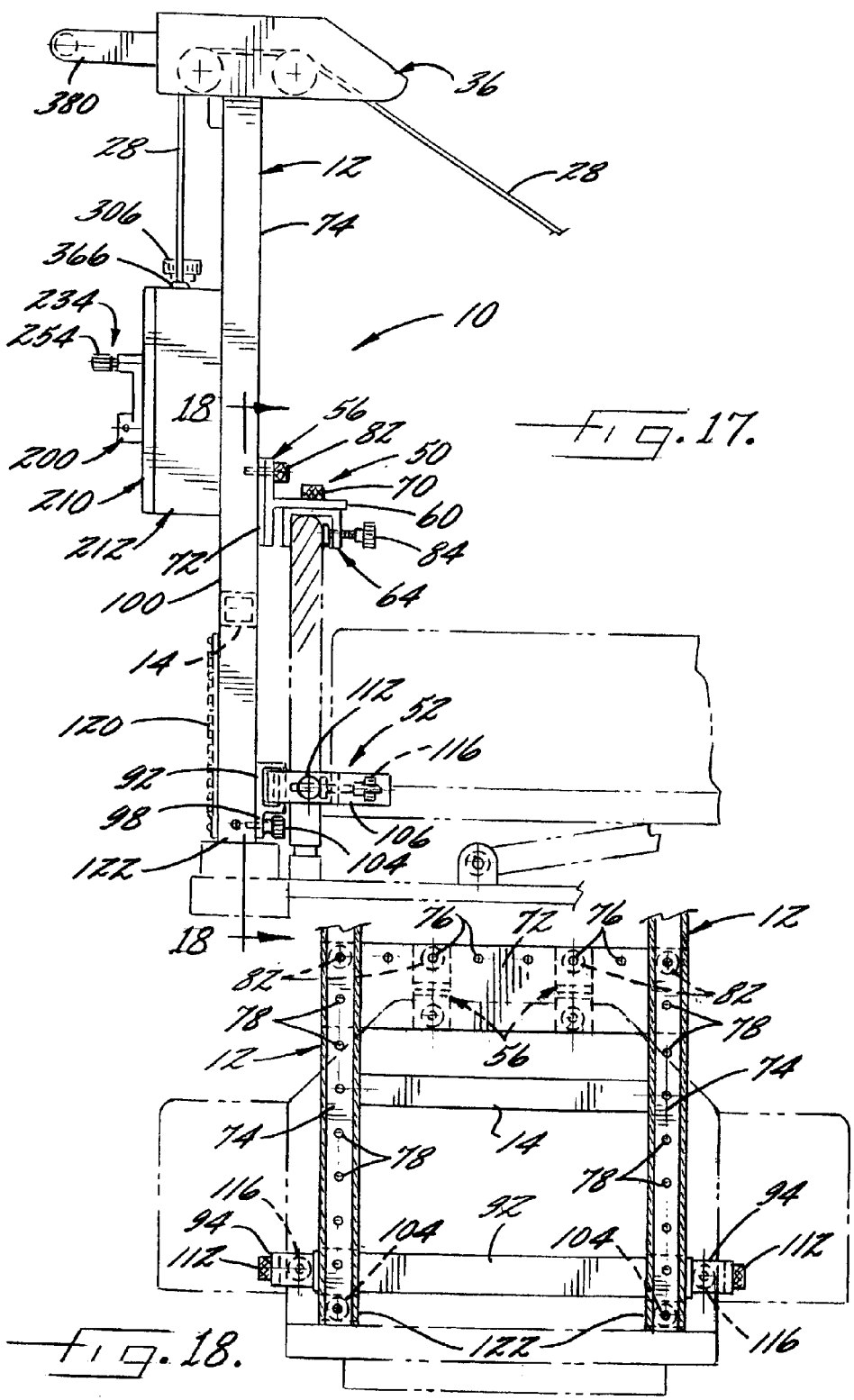

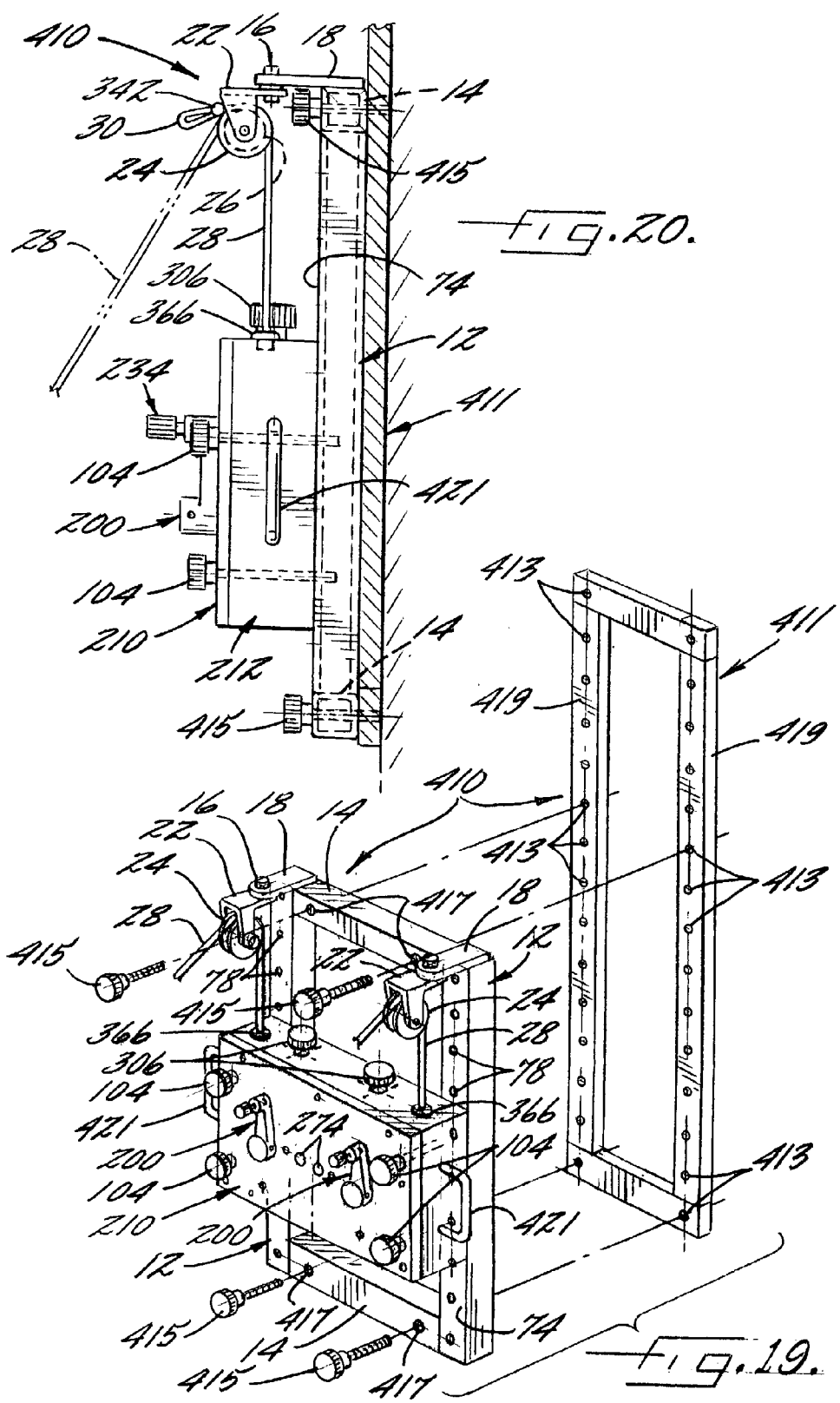

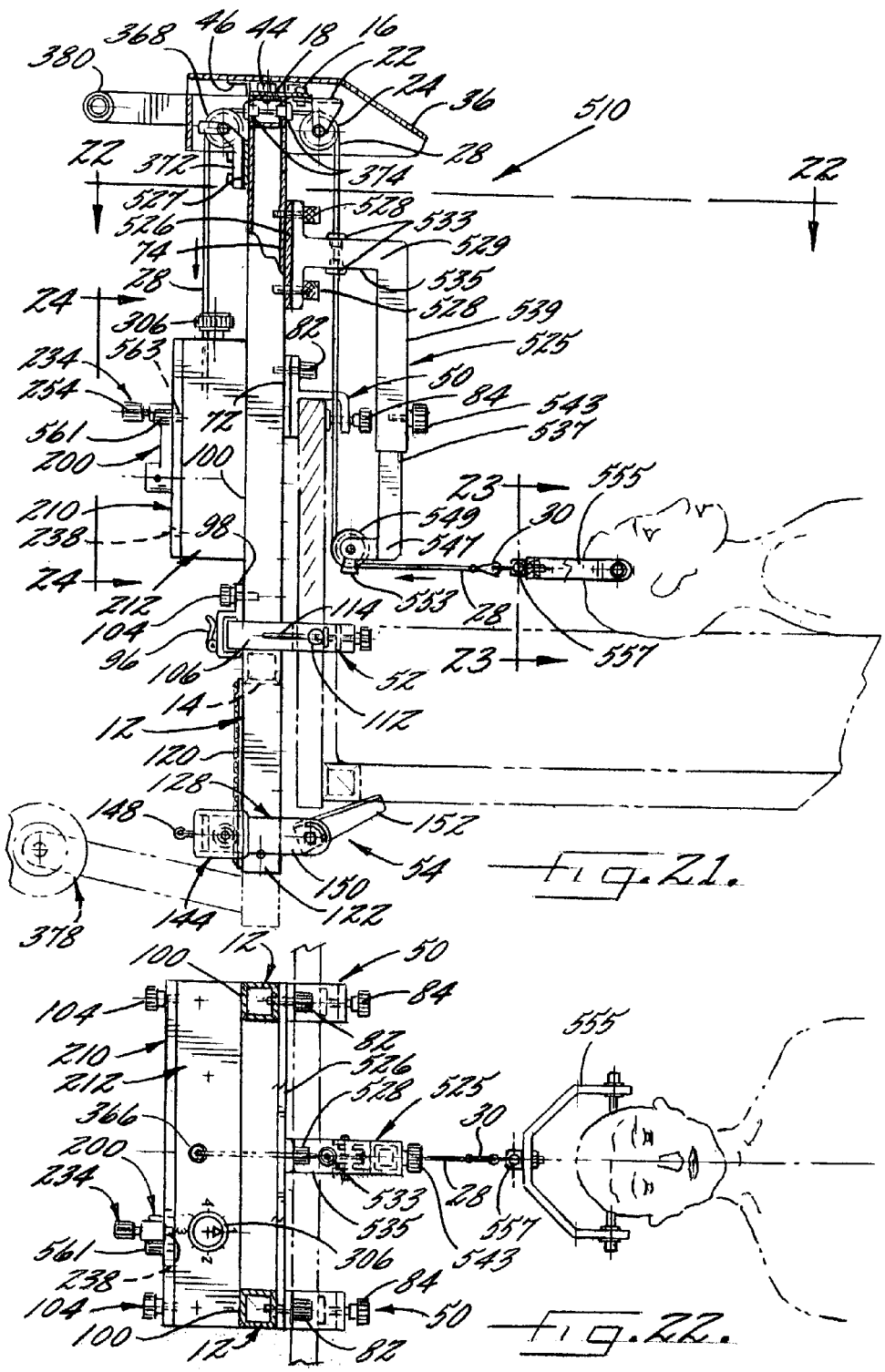

VERSATILE HEALTH CARE APPARATUS

FIELD OF THE INVENTION

This invention relates to an apparatus including a power spring, a pull-line connected to the power spring, and beneficially a guide wheel for the pull-line, useful for health care including physical therapy of a bed-ridden individual.

BACKGROUND OF THE INVENTION

As illustrated by U.S. Pat. No. 6,228,004 to one of the inventors of this invention, and U.S. Pat. Nos. 5,005,829 and 3,826,490, a health care apparatus for exercise or physical therapy of a bed-ridden individual is known. However, these apparatus are limited in that changing an exercise load, if possible, typically will involve adding or taking away weights or the like, or changing a resistance element.

Furthermore, there is a need for an improved health care apparatus for physical therapy of a bed-ridden patient. Among other things, it would be advantageous for such an apparatus to measure patient progress, and to have smooth, steady pull-line retraction. Otherwise, snap back could occur when a patient relaxes the tension exerted on the pull-line.

Moreover, there is a need for a health care apparatus that may be used to exert a desired pulling force on a patient's body, and maintain the pulling force. Such an apparatus would be useful for assisting spinal alignment, would be useful with a surgical retractor or the like, and have like uses.

In addition, it would be beneficial if a health care apparatus that can be used for physical therapy, or to exert a desired pulling force on a patient's body and maintain the pulling force, could be secured to a variety of suitable support structures and allowed the elevation of structural features to be easily changed. Moreover, ergonomic considerations should be taken into account.

SUMMARY OF THE INVENTION

In accordance with the present invention, there is provided a versatile health care apparatus that can be used for physical therapy, or to exert a desired pulling force on a patient's body and maintain the pulling force. In accordance with a first aspect of the invention, the inventive apparatus beneficially includes a support frame for a power spring, a pull-line connected to the power spring, and mounting apparatus that accommodates variation in support structures, and in particular variation in bed support structures. To this end, the mounting apparatus beneficially includes at least one adjustable, downwardly facing clamp and at least one adjustable cooperating clamp, and a rack and pinion mechanism is used to drive the cooperating clamp. Advantageously, the mounting apparatus further includes a side clamping assembly with telescoping arms, and the cooperating clamp is horizontally adjustable. This apparatus further includes, when used for physical therapy, a pair of ergonomically spaced apart guide wheels, and a second pull-line connected to a second power spring.

In accordance with a second aspect of the invention, the inventive apparatus beneficially includes a pull-line, and a rotatable pull-line wheel mounted on an axle and operatively connected to a power spring in connection with the axle, and the pull-line has an end in connection with the pull-line wheel. The power spring exerts torsional force upon the pull-line wheel. Beneficially, the apparatus further includes a guide wheel for the pull-line, and the guide wheel is mounted in a pulley block that may be pivotably mounted.

In accordance with this aspect of the invention, the exercise load for physical therapy may advantageously be increased by rotating the axle in an appropriate rotational direction, and restraining rotation of the pull-line wheel in the like rotational direction so that energy is applied to the power spring. Thereafter, an axle rotation-preventing element of the apparatus is engaged to maintain the power spring at that exercise load.

During physical therapy, rotation of the pull-line wheel upon the pull-line being extended by the patient, applies further energy to the power spring, it being recognized that the axle is prevented from rotation. This further energy is released as the pull-line is retracted. Advantageously, the apparatus may further include for smooth, steady pull-line retraction, a spring-biased brake shoe in frictional contact with the pull-line wheel for frictionally affecting rotation of the pull-line wheel, and optionally an inertia disc mounted on the axle for rotation with the pull-line wheel.

In accordance with the second aspect of the invention and use of an inventive apparatus to exert a desired pulling force on a patient's body, after connecting an opposite end of the pull-line with a device for exerting a pulling force on a patient's body, the axle is rotated in an appropriate rotational direction so that energy is applied to the power spring and so that a selected pulling force is exerted on the device by the torsion exerted by the power spring on the pull-line wheel. Thereafter, the axle rotation-preventing element is engaged to maintain that pulling force.

Illustrative devices for exerting a pulling force on a patient's body include a head-attachment structure that may beneficially be provided with a swivel bearing, and a surgical retractor. When used in an operating room, for instance with a surgical retractor, the inventive apparatus advantageously further includes a sterile shroud for enclosing the other apparatus structure. In any event, this inventive apparatus beneficially further includes an extensible guide member for the pull-line, for controlling the angle of the pulling force.

In accordance with the second aspect of the invention, a versatile health care apparatus that can be used for physical therapy, or to exert a desired pulling force on a patient's body, may further advantageously include an indicator of the exercise load or pulling force, as the case may be, driven by rotation of the axle. Advantageously, such an apparatus may further beneficially include a housing in which the pull-line wheel and the power spring are disposed, and an axle crank mounted to an end of the axle that extends through a wall of the housing, and the axle rotation-preventing element is a locking pin for locking the axle against rotation. Conveniently, the power spring is a flat coil spring mounted on the axle, with an end fixed to the axle and an opposite end connected to the pull-line wheel.

Additional advantages and beneficial features of the present invention are set forth in the drawing and detailed description, and in part will become apparent to those skilled in the art upon examination of the drawing and detailed description or may be learned by practice of the invention. In the drawing and detailed description, there are shown and essentially described only preferred embodiments of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention and illustrates preferred embodiments of the present invention.

FIG. 3 is a partially sectional rear view of the apparatus of FIGS. 1 and 2, with a portion of a housing cover plate broken away, and in phantom line, of bed support structure to which the apparatus is mounted;

FIG. 4 is a sectional top view of the mounted apparatus, taken substantially along line 4—4 of FIG. 3;

FIG. 7 is a partially sectional side view of the mounted apparatus of FIG. 3;

FIG. 8 is an exploded perspective view of a broken away portion of a frame member and a detachable wheel assembly;

FIG. 10 is an enlarged perspective view of an upper clamp of the apparatus of FIGS. 1 and 2;

FIG. 11 is a perspective view of the U-shaped portion of the clamp of FIG. 10;

FIG. 12 is an enlarged perspective view illustrating alternative attachment of the upper clamps of the apparatus of FIGS. 1 and 2 between the frame members;

FIG. 13 is an exploded enlarged perspective view of a portion of the adjustable clamp assembly illustrated in FIG. 9;

FIG. 14 is an exploded perspective view of the pull-line wheel and power spring housing and of the housing contents of the apparatus of FIGS. 1 and 2;

FIG. 15 is an exploded enlarged perspective view of the pull-line wheel, power spring and associated structure and axle of FIG. 14;

FIG. 16 is an exploded perspective view of a portion of the housing cover plate, the indicator wheel and its axle of the apparatus of FIGS. 1 and 2;

FIG. 17 is a side view like that of FIG. 7, of the mounted apparatus of FIGS. 1 and 2, with the FIGS. 9A, 9B clamp assembly and the wheel assembly removed, and in phantom line also showing associated obstructing structure of a particular type of hospital bed;

FIG. 18 is a sectional view of the mounted apparatus of FIG. 17, substantially along a line 18—18 of FIG. 17;

FIG. 19 is an exploded perspective view of a second preferred embodiment in accordance with the present invention;

FIG. 20 is a side view of the apparatus of FIG. 19 mounted to a wall;

FIG. 21 is a side view like that of FIG. 7, of a third preferred embodiment in accordance with the present invention, and in phantom line also showing a patient with his head attached to the apparatus;

FIG. 22 is a top sectional view taken substantially along a line 22—22 of FIG. 21;

DETAILED DESCRIPTION OF THE INVENTION

Figure 1:
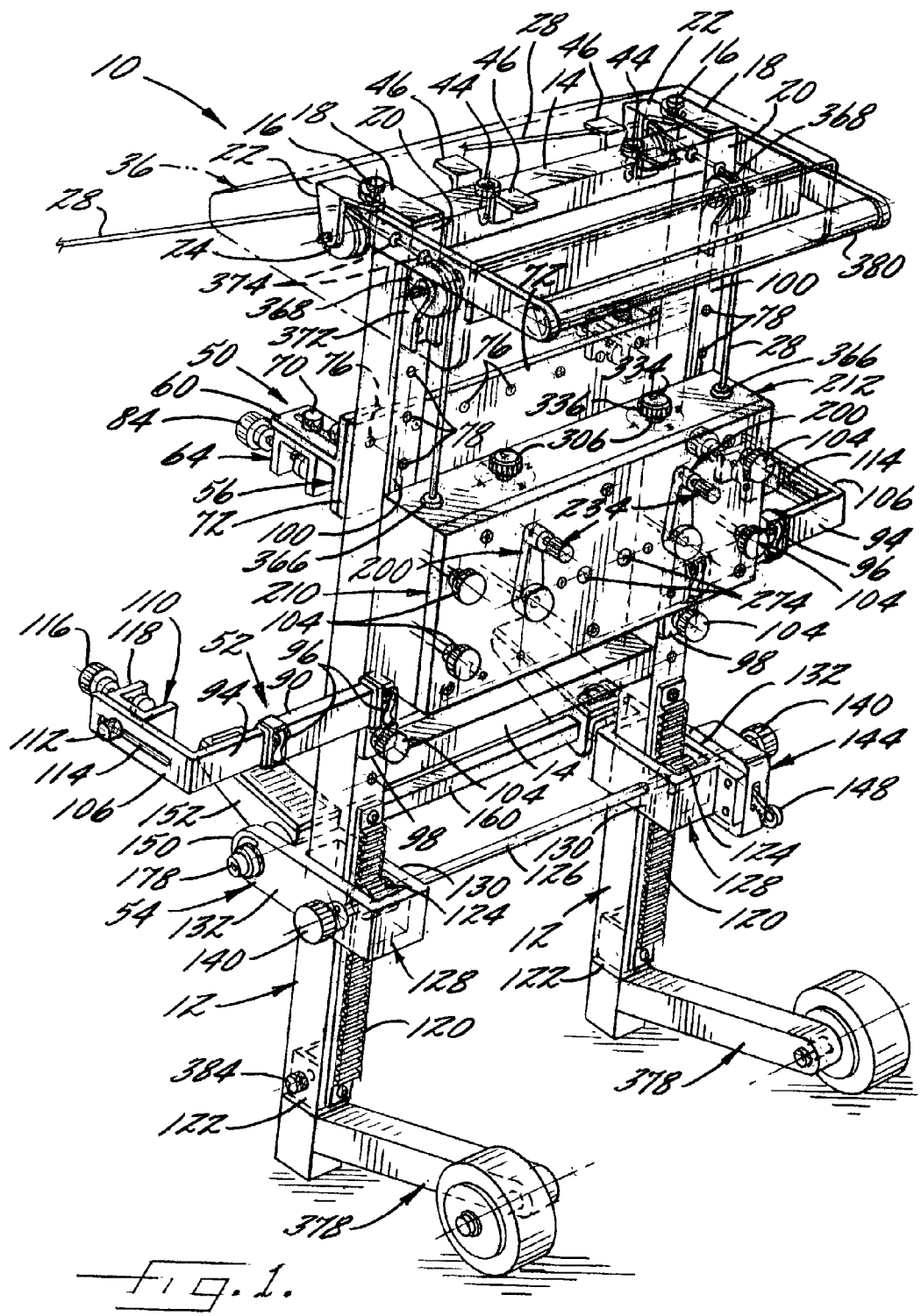
FIGS. 1 and 2 are perspective views of the rear and front of a first preferred embodiment in accordance with the present invention, with a protective cover shown in phantom line and in addition, in FIG. 2, shown in exploded relationship.

In accordance with the present invention, a versatile device is provided. As will be understood, terms such as "upwardly", "downwardly", "upper", "lower", "topside", "underside", "above", "vertical", "horizontal", "forward", "rearward", "front", "rear" and the like are relative, and have been particularly used with reference to the drawing to assist understanding.

With reference to FIGS. 1 to 18, a preferred health care apparatus 10 in accordance with the present invention, includes a support frame conveniently formed by a pair of spaced apart, generally parallel, elongated frame members 12 connected by spaced apart crossbars 14. Conveniently, as may be understood from FIGS. 4 and 6, for strength and for weight reduction, frame members 12 and crossbars 14 are elongated hollow tubes having a square cross-section.

Figure 2:
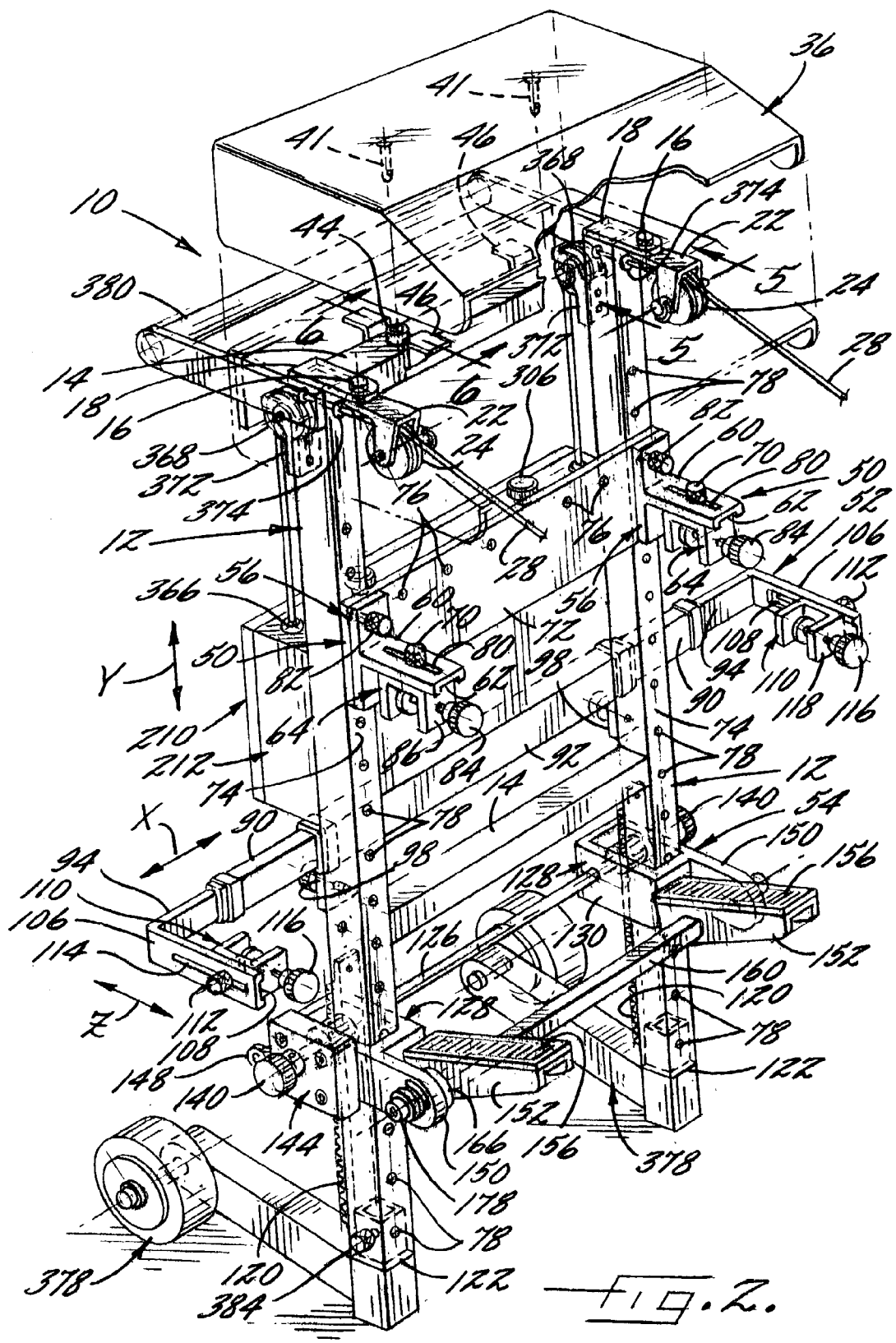

Referring particularly to FIGS. 1, 2 and 7, pivotably attached to frame members 12 via pivot shafts and threaded bolts 16 (best seen in FIG. 7), and a pair of spaced apart arms 18 conveniently fixed to upper ends 20 of the frame members, are a pair of spaced apart pulley blocks 22 in which guide wheels 24 are rotatably mounted. For further details concerning pivotable attachment of a pulley block to an arm using a pivot shaft or other fastener providing for pivotable attachment, and the resultant angular positionability, reference is made to U.S. Pat. No. 6,228,004, the pertinent portion of the disclosure of which is hereby incorporated by reference. Especially herein referenced in regard to advantages of angular positionability described therein, are FIGS. 6 and 10 of U.S. Pat. No. 6,228,004, of which FIG. 10 shows a pull-line directed by an angularly positionable, guide wheel in the direction of a side rail and the pull-line passing over a second guide wheel attached to the side rail. As will become understood and referring briefly to FIGS. 21–25, an angularly positionable, guide wheel is not always needed; rather, its usefulness depends upon the specific application to be made of an apparatus in accordance with the present invention. Likewise, referring again to U.S. Pat. No. 6,228,004, a useful pulley block does not need to be attached to an upper end of the support frame.

Figure 5:
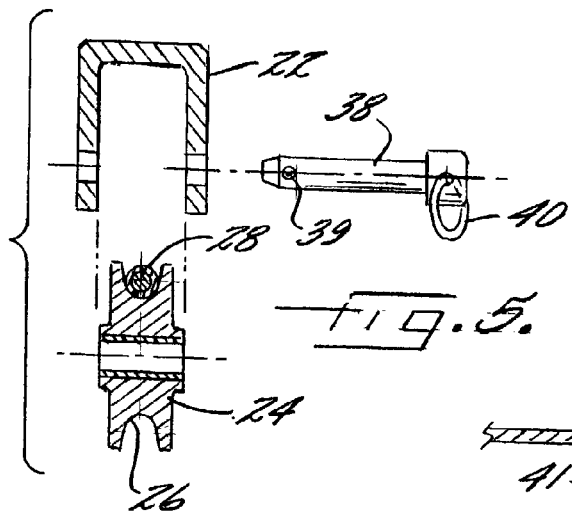
FIG. 5 is an enlarged exploded sectional view of a guide wheel, pulley block and an advantageous quick disconnect axle.

With reference particularly to FIG. 5, passing over each guide wheel and within a grooved rim 26 of each guide wheel, is a line 28, which is conveniently steel cable covered with plastic. Other suitable constructions may, of course, be used. The guide wheels are advantageously mounted on quick disconnect axles 38, each provided with a spring-biased retention ball 39 at one end and a pull ring 40 at an opposite end. In addition, as indicated, guide wheel rims 26 are advantageously deeply grooved for retention of lines 28.

With reference again to FIG. 7, a line end 30 is conveniently attached for physical therapy use, to a suitable grip or pull 32 by a clip 33 separated from the pull by a suitable length of a user's line 34. The length of a user's line will be selected based on factors including the particular body muscles to be exercised, and thus there will be user lines of different lengths to select from. It is intended that pulls 32 or the like will be used with the hands or feet.

Referring again in particular to FIG. 2, pull-lines 28 beneficially are ergonomically spaced apart a suitable distance, for instance about 16 to 18 inches, preferably about 17 inches, to benefit use together during physical therapy by an individual of typical physical build. This ergonomic spacing is based upon the shoulder width of an average adult male, but because of the angular positionability of guide wheels 24, will advantageously accommodate male or female body frames with more or less shoulder width.

As the pull-lines pass over guide wheels 24, the locations of which define the ergonomic spacing between the pull-lines, the pull-lines are beneficially centered on the respective frame member. Benefits include that each frame member 12 gives a user a visible reference point as to the origin of angular positionability of a respective pull-line. As can be appreciated from FIGS. 1 and 2, an advantageous protective cover 36, may block the line of sight of a user to the guide wheels, and hence the origin of angular positionability.

Figure 6:
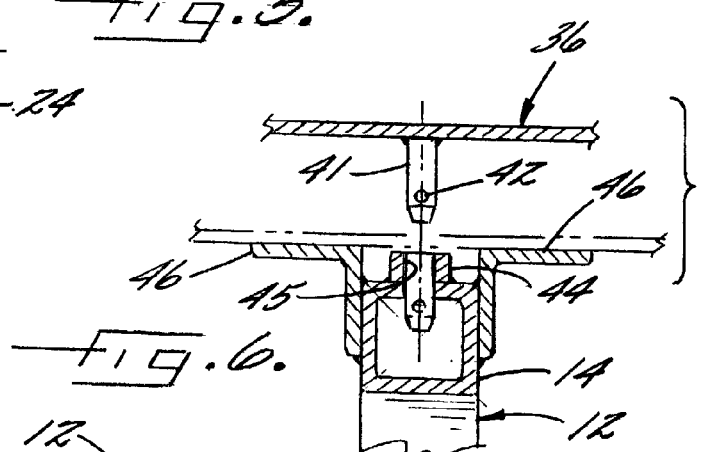
FIG. 6 is an enlarged exploded sectional view of a portion of the protective cover and a mounting boss.

Referring particularly to FIGS. 1, 2 and 6, cover 36 conveniently includes downwardly projecting mounting pins 41 each provided with a spring-biased retention ball 42 at its lower end, and upper crossbar 14 conveniently includes pin-retention bosses 44 each as best seen in FIG. 6, provided with a bore 45 through which the lower end of the respective mounting pin passes. For support of the mounted cover, support brackets 46 formed by generally horizontally extending arms, are conveniently fixed to upper crossbar 14. Cover 36 beneficially protects against pinch points.

With reference to FIGS. 1 to 4 and 7, for securing the apparatus to support structure in preparation for use, apparatus 10 beneficially includes adjustable mounting apparatus. Advantageously, the mounting apparatus accommodates variation in support structures, and in particular for certain applications, variation in bed support structures. To this end, the mounting apparatus beneficially includes a pair of spaced apart, downwardly facing, adjustable clamps 50, and a cooperating clamp assembly 54 that includes a hereinafter described, rack and pinion adjustment mechanism. Also advantageously provided are an adjustable side clamping assembly 52, and horizontal adjustment of the upwardly facing, cooperating clamp. However, other means may be used to secure an apparatus in accordance with the invention, to useful support structure.

Referring also to FIGS. 10 to 12, downwardly facing, U-shaped clamps 50 each beneficially include a slotted, generally T-shaped bracket 56 provided with at least one mounting aperture 58 and that includes a generally horizontally disposed arm 60 provided with a guide channel 62 on its underside; a U-shaped member 64 that includes on its topside a sliding plate 66 provided with a threaded bore 68 and sized to snugly slide within the guide channel yet have adequate mechanical clearance for facile movement; and an adjustment bolt 70.

For adjustment of clamps 50 along an x-axis as indicated in FIG. 12, an adjustment plate 72 conveniently extends from over a front wall 74 of one frame member to over a front wall 74 of the other frame member, and is provided along the x-axis with a plurality of suitably spaced apart threaded apertures 76. For elevational adjustment of plate 72 and clamps 50 (a y-axis is indicated in FIG. 12), each elongated frame member is beneficially provided along its length with a plurality of suitably spaced apart threaded apertures 78. For forward/rearward adjustment of each U-shaped member 64 along a z-axis as indicated in FIG. 12, and tightening of the U-shaped member in a selected z-axis position, a threaded end of adjustment bolt 70 conveniently extends through a bracket slot 80, which advantageously leads to guide channel 62, and into the sliding plate of the U-shaped member.

Threaded thumb screws 82 secure clamps 50 and the adjustment plate in the selected positions. A clamp bolt 84 extends through a wall 86 of each U-shaped member 64, for clamping action. As can readily be recognized and with reference again to FIGS. 1 to 4 and 7, depending upon considerations including the shape and dimensions of the support structure to which the U-shaped clamps are to be attached, the U-shaped clamps could be directly attached to frame members 12 and the adjustment plate could be eliminated.

With continued reference to FIG. 2 in particular, side clamping assembly 52 conveniently includes for adjustment along the x-axis, a first pair of telescoping arms 90 slidably disposed to extend from within an elongated sleeve 92, and a second pair of telescoping arms 94 slidably disposed to extend from within arms 90. With pivotably mounted handles 96 in a lock position as shown in FIG. 3, arms 90,94 are frictionally held in selected x-axis positions. Beneficially, when telescoping arms 90,94 are in a fully retracted position (not illustrated), the apparatus width is significantly reduced to approximately the width of the spaced apart frame members.

For elevational adjustment of the side clamping assembly (the y-axis is indicated in FIG. 2), the elongated sleeve conveniently includes, referring also in particular to FIG. 1, a pair of mounting brackets 98 suitably spaced apart for alignment with frame members 12, and the frame members include threaded apertures 78. Threaded thumb screws 104 conveniently secure the side clamping assembly to the frame members at a selected vertical position. As can be appreciated from FIGS. 1 and 3, apertures 78 conveniently define a vertically disposed midline of each frame member.

Referring also to FIGS. 17 and 18, apertures 78 advantageously allow a side clamping assembly to be attached not only to rear walls 100 of the frame members but also to frame member front walls 74. Using apertures 78, a side clamping assembly can be attached to the frame members in an inverted position in which the mounting brackets are positioned above the elongated sleeve (see FIG. 21).

For forward/rearward adjustment along the z-axis with reference again to FIG. 2, telescoping arms 94 are generally L-shaped so as to include side arms 106, and the side clamping assembly is otherwise beneficially constructed similar to clamps 50 in that side arms 106 each include a guide channel 108, in that each U-shaped member 110 includes a sliding plate (not shown) provided with a threaded bore (not shown), and in that a threaded end of each adjustment bolt 112 extends through a bracket slot 114 and into the sliding plate of the respective U-shaped member. A clamp bolt 116 extends through a wall 118 of each U-shaped member 110, for clamping action.

With continued reference to FIGS. 1 to 3 and 7, upwardly facing clamp assembly 54 beneficially cooperates for its elevational adjustment, with a pair of elongated racks 120 each conveniently in alignment with the length of the respective frame member and secured to rear wall 100 thereof, and extending upward from the lower end 122 of the respective frame member so as to allow for a clamp position close to the lower ends of the frame members. To this end and referring also to FIG. 13, the adjustable clamp assembly advantageously includes a pair of spaced apart pinion gears 124 each engaged with its respective rack 120 and each conveniently mounted on a rotatable round shaft 126. Rotatable shaft 126 conveniently extends through, and is supported by, a pair of spaced apart, linear sliding brackets 128, each of which is advantageously disposed around, and in sliding contact with, its respective frame member. The pinion gears are each conveniently disposed between opposing side walls 130,132 of the respective linear sliding bracket, and provided with a keyway slot 134. Conveniently, rotatable shaft 126 is provided at each end 136 with keyway slots 138, and a control knob 140 is disposed at each end 136, and receives the respective end, of the rotatable shaft within a bore (not shown) provided with a keyway slot (not shown). With reference specifically to FIG. 13, set screws 142 in combination with keys (not shown), and the keyway slots of the rotatable shaft, pinion gears and control knobs, conveniently align and secure the pinion gears and control knobs on the rotatable shaft, for transmission of torque.

Beneficially, vertical adjustment of clamp assembly 54 is controlled by a two pawl, ratchet clutch 144, conveniently of a type commercially available from Lowell Ratchet Clutches. Conveniently, the ratchet clutch is disposed between one of the control knobs and side wall 132 of one of sliding brackets 128, and mounted to wall 132. Alternatively, the ratchet clutch could be mounted on rotatable shaft 126 in another suitable location such as to wall 130. Clutch 144 conveniently includes a gear wheel 146 shown in FIG. 7, having a centrally located mounting aperture with a keyway slot (not shown) that is aligned by the respective key with respective keyway slot 138 of the rotatable shaft. Clutch 144 further advantageously includes a pair of spaced apart, spring-loaded pawls (not shown) for engagement with gear wheel 146, and a pivotably mounted lever 148 disposed between the pawls for disengagement of the pawls from the gear wheel.

When lever 148 is in a first position for instance as exemplified in FIGS. 1 and 2, lever 148 disengages one of the pawls from the gear wheel so that only one pawl remains in engagement with the gear wheel, and downward movement of the clamp assembly by rotation of either control knob is permitted but upward movement is blocked. In a second and opposite position of lever 148 for instance as illustrated in FIG. 7, the lever disengages the previously engaged pawl from the gear wheel, and the lever position allows the previously disengaged pawl to re-engage the gear wheel, and upward movement of the clamp assembly by rotation of either control knob is permitted but downward movement is blocked. This lever position advantageously allows the clamp assembly to be positively adjusted upwards into, and locked in, a selected vertical position. In a third position of lever 148 (illustrated in FIG. 21) in which the lever is typically disposed between the first and second positions, both pawls are in engagement with the gear wheel and movement of the clamp assembly in either direction is prevented. This lever position is advantageous, for example, for transport of the apparatus.

It has been illustrated that the first and second positions of the lever are down and up, respectively. However, it will be recognized that whether a lever is down or up for the result stated, depends upon factors including the construction of the ratchet clutch used.

In a variation, a ratchet clutch with only one pawl may be used. In a first position, the lever would disengage the pawl from the gear wheel. This lever position would allow the clamp assembly to be adjusted upward or downward. In a second position, the position of the lever would allow the pawl to be in engagement with the gear wheel, and upward movement of the clamp assembly by rotation of either control knob is permitted, but downward movement is blocked. This lever position is advantageously similar in result to the second position discussed earlier. As the skilled artisan will also readily recognize, other types of ratchet clutches could be used, for instance, a two pawl ratchet clutch with a neutral third position, provided that the ratchet clutch selected, provides for a combination of upward movement but blocked downward movement of the clamp assembly.

With particular reference to FIG. 13, conveniently extending from each sliding bracket 128 in the forward z-axis direction previously described with respect to clamps 50, is a bracket extension 150, to which an elongated jaw 152 for engagement with support structure, is pivotably connected. Advantageously disposed on an upper face of each elongated jaw is a contact pad 156 suitably made of rubber or a like compressible material for assisting in the engagement as the jaw is positively upwardly adjusted. Jaws 152 are each conveniently provided with a square mounting aperture 158 and mounted on a cross-sectionally square shaft 160. Round ends 162 of shaft 160 conveniently extend through round apertures 164 of spaced apart bracket extensions 150, thereby providing support for shaft 160 and the elongated jaws. Conveniently securing shaft 160 to the bracket extensions are screws 178, which extend through washers 180 and wave washers 182, and into threaded bores 184 (only one shown) in the shaft ends.

Conveniently disposed adjacent each bracket extension 150 and mounted on shaft 160 between the respective extension and elongated jaw, is a pin ring 166 provided with a square mounting aperture 168. To limit rotation of shaft 160 to pivotable movement and for control of the extent of the pivotable movement of the shaft and thus of the elongated jaws, an adjustment control pin 170 conveniently extends from a pin ring face 172 in the direction of, and into, an arc-shaped aperture 174 of the adjacent bracket extension. To maintain the control pin within the arc-shaped aperture, side movement of the respective pin ring 166 on shaft 160 is beneficially prevented. Set screws 186 conveniently prevent side movement of the pin rings.

Figure 9A:
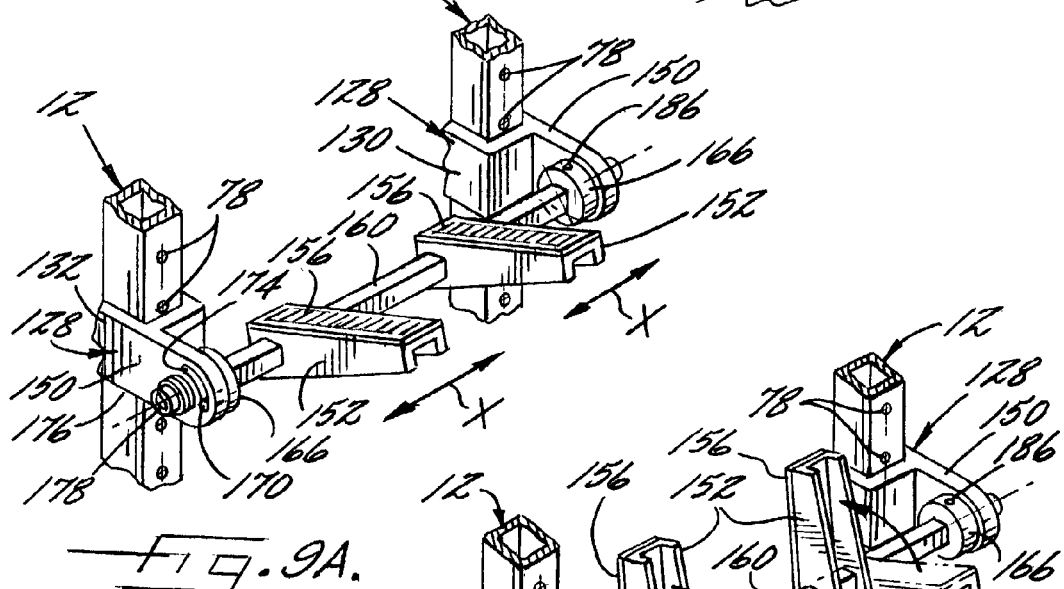
FIGS. 9A and 9B are perspective views of a broken away portion of the apparatus of FIGS. 1 and 2, illustrating the pivotable jaws of a clamp assembly in an engagement position and stow position, respectively.
Figure 9B:
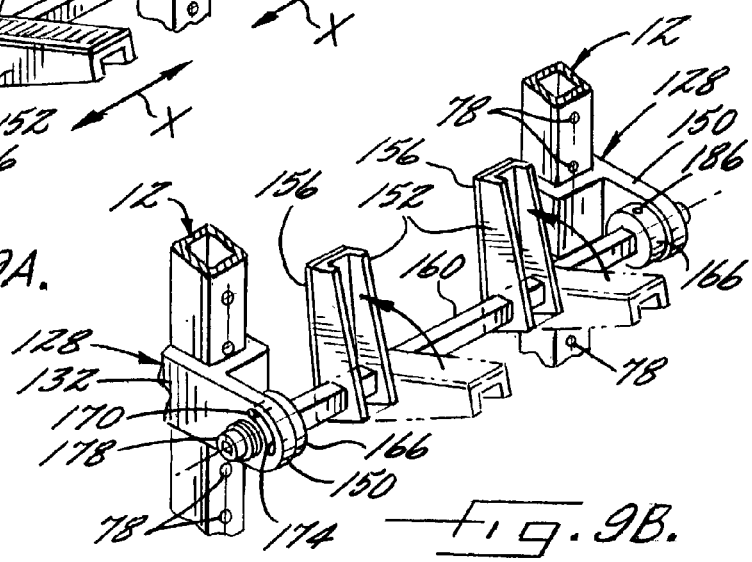

The aperture arc is of an appropriate location and extent so that a desired range of pivotable movement of the elongated jaws is obtained as illustrated in FIGS. 9A and 9B. Referring now specifically to FIGS. 9A and 9B, when control pin 170 is at one end of arc-shaped aperture 174 as shown in FIG. 9A, the elongated jaws are held in an upwardly angled (relative to a plane defined by a bottom surface 176 of sleeve-like bracket 128), open position for engagement; whereas, when the control pin is at the other end of the arc-shaped aperture as shown in FIG. 9B, the elongated jaws are disposed in a closed or stow position.

Beneficially, the elongated jaws, when not engaged with a support structure, are able to freely slide on the pivotably mounted shaft along the x-axis, as illustrated in FIG. 9A. As can be readily recognized, if desired, only one, or more than two, jaws could be used, and if only one jaw were used, that jaw could have any suitable width (it being understood that the x-direction defines jaw width). Moreover, a single pin ring, control pin and arc-shaped aperture would be mechanically sufficient for control of the pivotable movement of the jaws.

Upward vertical adjustment of clamp assembly 54 for engagement with a target support structure, has been illustrated in FIG. 7 as utilizing an up position of lever 148, whereas downward vertical adjustment has been illustrated in FIGS. 1 and 2 as utilizing a down position of lever 148. Whatever the appropriate lever position, when the lever is in that position, either of the control knobs may be appropriately rotated to produce the desired upward or downward vertical adjustment. With reference to FIG. 2, CCW rotation of control knob 140 adjacent ratchet clutch 144 would rotate rotatable shaft 126 CCW so as to cause the pinion gears to rotate CCW, thereby producing downward vertical movement. Referring again to FIG. 7, with the elongated jaws (only one shown) held in an upwardly angled, open position by control pins 170 (only one shown), CW rotation of the control knob (not shown) adjacent ratchet clutch 144 would rotate the rotatable shaft CW so as to cause the pinion gears to rotate CW, thereby producing upward vertical movement of the elongated jaws until engagement is obtained with the target support structure. After engagement with the support structure, the control lever could be left in an up position as illustrated in FIG. 7, or could be moved to a position in which both upward and downward movement are blocked.

It can be appreciated that because of the upwardly angled position of elongated jaws 152 when engaged, reach of jaws 152, unlike the reach of U-shaped clamps 50 or side clamping assembly 52, does not necessarily require adjustment to adapt to a greater or lesser distance between frame members 12 and the target support structure. Instead, the locus of engaged contact of the support structure on the jaw pad changes. Given this benefit, one might use as downwardly facing clamps in place of U-shaped clamps 50, a clamp assembly like that of clamp assembly 54 but disposed in a upside down position so that the elongated jaws are held in a downwardly angled position for engagement, with a second set of racks secured to the frame members.

In use, apparatus 10 is wheeled up to a support structure which may be a bed having a headboard or footboard and associated frame structure, as indicated in phantom in FIGS. 3 and 7, and vertically adjustable jaws 152 are set in an upwardly angled, open position. If the bed is vertically adjustable, the bed may be lowered in elevation until the top of the headboard or footboard is lower than upper clamps 50. After engagement of the downwardly facing clamps, opposing clamp assembly 54 is raised using the rack and pinion, and an appropriate position of the ratchet clutch lever until engagement with the target support structure. Side clamping assembly 52 may be adjusted and attached to the support structure before or after engagement of clamp assembly 54.

With continued reference to FIGS. 3, 4 and 7, after apparatus 10 has been secured to suitable support structure, the apparatus may then be readied for use. To this end and referring also in particular to FIGS. 14 to 16, the apparatus is beneficially provided with a load-adjusting feature. The load-adjusting feature advantageously includes an axle crank 200 conveniently mounted to an end 202 of a rotatably mounted axle 204 that extends through a bushing 206 disposed in an aperture 208 of a wall 210 of a housing 212, and a power spring 214. By "power spring" is meant for purposes of this description, a spring that stores and releases energy. Conveniently, the power spring is a flat coil spring mounted within protective housing 212 on axle 204 and fixed to the axle at one end by a tang 216 received within an axle slot 218 (best seen in FIG. 15). Conveniently, wall 210 is a removable housing cover plate, and a set screw 220 fixes the axle crank to axle end 202. An opposite axle end 222 extends through an aperture 224 of an opposing housing wall 226, and is retained by a retaining ring 228 disposed in a circumferential axle groove 230.

Referring particularly to FIGS. 14 and 15, as rotatably mounted axle 204 is rotated CW by CW rotation of the load-adjusting axle crank, the CW-winding ("right handed") power spring is increased in tension, it being understood that increase in the spring tension requires that an opposite spring end 232 is restrained from like CW rotation. Conversely, CCW rotation of the axle crank unwinds the right handed, power spring. A skilled artisan will readily recognize with reference to FIG. 3, that the other power spring (not shown) is CCW-winding ("left handed"), and that CCW rotation of its axle crank 200 increases its tension.

With continued reference to FIGS. 7 and 14 in particular, the load-adjusting feature beneficially further includes for the purpose of maintaining the increased spring tension, a spring loaded-locking pin 234 that locks the axle against rotation. Conveniently, the locking pin extends through an end 236 of the axle crank, and one or more locking pin apertures 238 are provided in cover plate 210 to receive an end 240 of the locking pin, and are suitably spaced apart, for instance, at the 12 o'clock and 6 o'clock positions as illustrated. A locking pin spring 242 conveniently disposed around a shaft 244 of the locking pin and retained in a bore 246 (best seen in FIG. 7) of axle crank end 236 by a retaining ring 248 disposed in a circumferential shaft groove 252, biases the locking pin toward the cover plate. Conveniently, a locking pin knob 254 allows the locking pin to be grasped by a user and locking pin end 240 to be disengaged from the housing cover plate for adjusting the spring tension.

It will be appreciated from the description that follows, that during use of the apparatus, axle 204 is locked against rotation by engaging locking pin 234 or is otherwise prevented from rotation, regardless of whether a load adjustment has been made. Furthermore, it will be understood that rotation of the hereinafter-described pull-line wheel upon the pull-line being extended, applies energy to the power spring, and that this energy is released as the pull-line is retracted. Likewise, it will be readily recognized by one skilled in the art that other convenient ways to prevent axle 204 from rotation include, for instance, the use of friction.

With continued reference in particular to FIGS. 3, 14 and 16, the load-adjusting feature advantageously further includes an indicator 256 responsive to load adjustment and driven by rotation of axle 204. Conveniently to this end, within housing 212, a drive gear wheel 258 is mounted on, and fixed to, a splined portion 260 of axle 204, and is in engagement with relatively larger, indicator gear wheel 256 mounted on a rotatably mounted bushing 262 through which a shoulder bolt 264 extends and is threaded into a threaded bore 266 in the housing cover plate. Indicia illustratively indicated by numbers in FIG. 3, on a face 270 of the indicator gear wheel facing the cover plate, indicate load. This feature advantageously further includes, because of location of the indicator within the housing, a sight aperture 274 appropriately located in the cover plate for registering with the indicia. If desired, a transparent lens (not shown) can be retainably disposed within the sight aperture to seal the aperture, and may be also used for magnification. Thus, as axle 204 is rotated by the load-adjusting axle crank and the flat coil spring is wound or unwound, indicator wheel 256 is rotated and an appropriate indicium is displayed through sight aperture 274.

It will be appreciated by one skilled in the art that an appropriate gear ratio of the indicator wheel to the conveniently smaller drive wheel will be selected based upon considerations including the load resistance of the power spring used, and power springs of different load resistance can be expected to be useful depending upon the intended use, and in the case of a physical therapy device, the typical range in strength of intended users. Thus, referring specifically to FIG. 14, the indicia may conveniently be keyed to a load chart decal 276 appropriate for the power spring and affixed to a face 278 of the housing cover plate.

Beneficially, the load-adjusting feature allows patient progress to be measured. More specifically, the power spring can be adjusted to a specific load prescribed by a physician and indicated by the indicator wheel, and progress can be measured, for instance, by the number of exercise repetitions at that load before fatigue. Thereafter, the power spring load may be increased to a greater prescribed load indicated by the indicator wheel, and the number of exercises repetitions at that load before fatigue, charted; and so forth.

With reference now to FIGS. 7, 14 and 15, conveniently mounted within protective housing 212 on rotatably mounted ball bearings 280 through which axle 204 extends, is a pull-line supply/storage wheel 282 to which an end (not shown) of the pull-line is fixed. As previously indicated, wheel 282 may be rotated independent of any rotation of axle 204. Conveniently press fit into a face 284 of wheel 282, and extending from face 284 in the direction of power spring end 232, and capturing the power spring end is anchor pin 286, which extends into a curl 288 at the power spring end. As a result of this connection between wheel 282 and the power spring, wheel 282 is under torsion provided by the power spring. An opposing force is provided by the pull-line.

Conveniently mounted on one of rotatably mounted ball bearings 280, and disposed between pull-line wheel 282 and the power spring, is an optional inertia disc 294. Anchor pin 286 conveniently extends through an appropriately located inertia disc aperture 296 so that the inertia disc rotates with the pull-line wheel. Beneficially, disc 294 increases the inertia of the pull-line wheel by its added mass, and thereby retards rotational acceleration or deceleration of the pull-line wheel.

Referring now to FIGS. 3, 4, 7 and 14 in particular, apparatus 10 beneficially includes a damping assembly 300 for frictionally affecting the rotation of the pull-line wheel. Damping assembly 300 conveniently includes a spring-biased, brake shoe 302 disposed at least in part within, and guided in the direction of the pull-line wheel by, a damping assembly housing 304 attached to protective housing 212. Conveniently, a threaded adjustment bolt 306 extends through a threaded aperture 308 (shown in FIG. 14) in an upper wall 312 of housing 212 for pressure contact on an end 314 of a helical compression spring 316 disposed within housing 304. An opposite spring end 318 is in pressure contact with a brake shoe face 320 opposite to an arcuate brake shoe face 322 in friction contact with rim 324 of the pull-line wheel. In this way, the brake shoe is conveniently biased into friction contact with the pull-line wheel rim, and the pressure of the friction contact can be increased or decreased by appropriate rotation of adjustment bolt 306 to respectively increase or decrease the extent of the adjustment bolt within damping assembly housing 304.

Advantageously, the damping assembly and inertia disc resist rotational motion of the pull-line wheel in either direction. When the pull-line is being pulled, the resistance assists smooth feed of the pull-line. Conversely, when a user relaxes the tension exerted on the pull-line, the resistance assists smooth, steady pull-line retraction and thereby prevents snap back.

Beneficially, with reference particularly to FIG. 4, the damping assembly includes indicator marks 333 illustrated as numbers on upper housing wall 312, and an indicator mark 334 on a head 336 of the adjustment bolt, for instance on an upper surface as shown. The rotational adjustment needed to apply the desired friction to the pull-line wheel, will vary depending upon factors including the compressive resistance of the spring selected, the frictional resistance desired, and the wear of brake shoe face 322. Thus, these indicator marks may be used to indicate the degree of rotational adjustment of adjustment bolt 306 and the wear of brake shoe face 322. For optimal use, the brake shoe should be periodically replaced.

As previously indicated and with continued reference to FIGS. 3, 7 and 14, as rotatably mounted axle 204 is rotated, the power spring load is increased or decreased, so long as spring end 232 is restrained from like rotation. Advantageously, restraint of the spring end may be effected by restraint of pull-line wheel rotation. With particular reference to FIG. 7, to provide the restraint, pull end 30 of the pull-line may be adapted to block retraction of the pull-line end through a throat formed by the respective guide wheel and pulley block. Conveniently, for example, pull end 30 may be provided with an enlarged member 342, for example a ball through which the pull-line extends and that is also used to provide a loop at the pull line end, of sufficient size to block the retraction. It will be readily recognized by a skilled artisan that other convenient ways may be used to restrain pull-line retraction. For instance, pull-line end 30 could be temporarily secured to the shaft of clamp bolt 84.

Now referring to FIGS. 3 and 14, and with particular reference to pull-line wheel 282, CW-winding power spring 214 and CCW pull-line feed (the right handed spring/wheel in FIG. 3), when axle 204 is rotated CW, the end of the power spring fixed to the axle, rotates CW with the axle. However, because pull-line end 30 is captured in the pulley block throat (or otherwise restrained from retraction) and the pull-line wheel therefore cannot rotate CW, spring end 232 is restrained by anchor pin 286 from CW rotation. As a result, the CW-winding power spring is wound and the power spring load is increased. On the other hand, when the power spring load has previously been increased by winding the power spring and axle 204 is rotated CCW to decrease the power spring load, so long as the CW-winding power spring remains under its own tension, the pull-line wheel is biased in the CW direction by the power spring, yet prevented from CW rotational movement by restraint of pull-line end 30 from retraction. As a result, a degree of unwinding of the CW-winding power spring occurs, and the power spring load is reduced.

Figure 24:
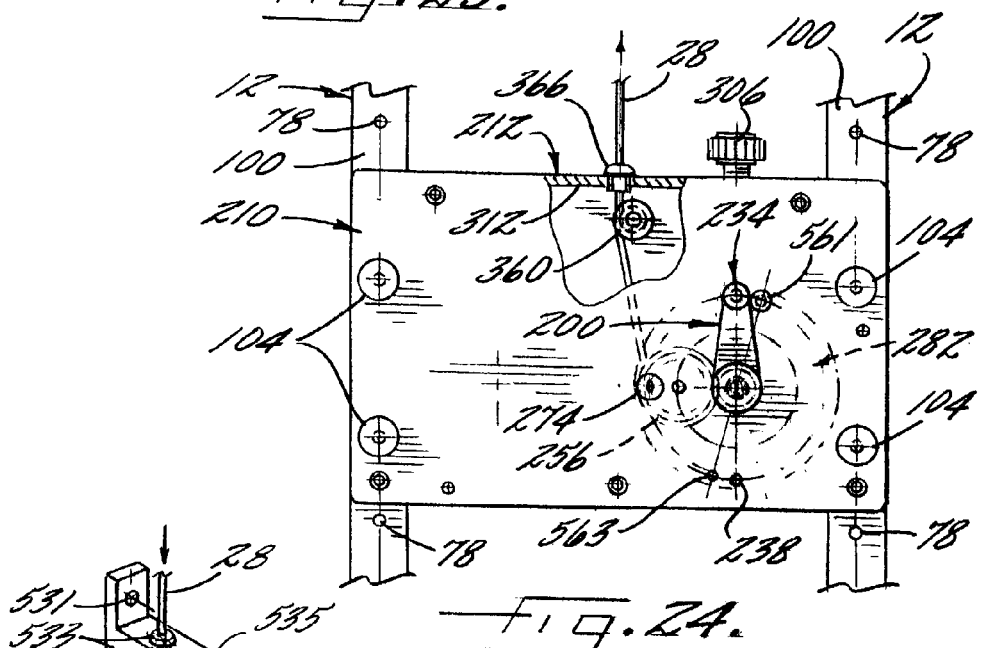
FIG. 24 is an enlarged view taken substantially along a line 24—24 of FIG. 21, with a portion of a housing cover plate broken away.

With reference now to FIG. 3 in particular, pull-line wheel 282 with CCW-winding power spring and CW pull-line feed (left-handed spring/wheel; power spring not shown), is indicated. As a skilled artisan will readily recognize, reverse rotational movement of the axle of the left-handed pull-line wheel and its CCW-winding power spring to that just described, respectively increases and decreases the power spring load. It will further be recognized that the left-handed/right-handed order shown in FIG. 3 could be reversed and the pull-lines could exit housing 212 between damping assembly adjustment bolts 306, if desired, or that other modifications can be made as illustrated in FIG. 24 and later described, or that other types of power storing/releasing members could be used.

Furthermore, an application of sufficient frictional force by damping assembly 300 to the rim 324 of the pull-line wheel to overcome the torsion exerted by the power spring on the pull-line wheel, may be used to prevent any rotational movement of the pull-line wheel and hence of spring end 232 when adjusting the power spring load. This alternative may be used in place of, or in addition to, restraint of pull-line end 30 from retraction.

With continued reference particularly to FIGS. 3 and 14, alignment of the housing cover plate with housing 212 is conveniently provided by alignment pins 350 and corresponding alignment pin apertures 352 in the cover plate. Threaded bolts 354 (only one shown in FIG. 14) fasten the cover plate to the housing.

Referring also to FIG. 7, housing 212 is suitably attached to rear walls 100 of the frame members by threaded thumb screws 104, which extend through mounting apertures in the cover plate and through mounting bosses 358, and are threaded into threaded apertures 78. Because as previously described, apertures 78 are suitably spaced apart along the length of the frame members, vertical location of housing 212 and its contents on the support frame can be adjusted. Beneficially, as can be best appreciated from FIG. 7, because downwardly facing clamps 50 and clamp adjustment plate 72 are attached to the front walls of the support frame, whereas housing 212 is attached to the rear walls of the support frame, increased elevational adjustability of clamps 50, the clamp adjustment plate and housing 212 is provided, as well as independent adjustability. Also, it will be appreciated that, if appropriate, housing 212 and its contents can be demounted and replaced with a like housing having power springs with relatively greater or less resistance.

Between the pull-line wheel and respective guide wheel 24, each pull-line conveniently passes over a housing exit-directing wheel 360 rotatably mounted on an axle 362 seated in housing wall 226, exits the housing through a bearing 366 in housing upper wall 312, and vertically ascends the rear wall 100 of its respective frame member. As can be appreciated from FIG. 3 in particular, the exit-directing wheel conveniently directs the pull-line so that its ascent follows the rear wall midline defined by apertures 78. At the top of the ascent, each pull-line conveniently passes over a directing wheel 368 rotatably mounted in a pulley block 372 fixed to the rear wall of the respective frame member, and then passes through the respective frame member being guided by a pair of spaced apart, rear wall and front wall bearings 374, to reach guide wheel 24.

Referring again to FIGS. 1 and 2, apparatus 10 further conveniently includes wheel assemblies 378, useful for moving the apparatus along a floor or like surface. Conveniently, the wheel assemblies are individually attached to the lower ends 122 of the frame members and extend in a direction that will be away from support structure. A pull handle 380 conveniently is attached to upper ends 20 of the frame members and extends in the same direction as the wheel assemblies. When the apparatus is not secured to support structure, the frame members conveniently have a generally vertical orientation in which as illustrated in FIG. 1, the frame members are oriented several degrees from a true vertical position in the direction of the wheel assemblies. As a result, the apparatus will conveniently have its center of gravity located away from a true vertical position and in the direction of the counterbalancing wheel assemblies, for the benefit of the apparatus being free-standing when not mounted, or of a person pulling the apparatus using pull handle 380 when moving the apparatus.

As indicated in FIG. 7, when apparatus 10 is mounted, wheel assemblies 378 may be off the floor. However, this is not a necessary feature of the present invention. Moreover, in certain cases, it will be beneficial for an apparatus in accordance with the invention, to remain in supporting contact with a floor or like supporting surface during use.

Referring particularly to FIG. 8, the wheel assemblies beneficially are releasably attached to the frame members. To this end, for each wheel assembly, a thumb screw 384 conveniently extends through a side wall aperture in the lower frame end and into a threaded side wall aperture 388 in a mating sleeve 390 having a like square cross-section and reduced in size to fit within the lower frame end. Alternatively, a spring-biased, retention ball could be used to provide the releasable attachment.

If supporting contact of the apparatus with a supporting surface is desired, the wheel assemblies may be removed, and extensible legs (not shown) each having a mating sleeve like sleeve 390, may be advantageously inserted into the lower frame ends. The insertion, as well as contact with the supporting surface, can be assisted by any vertical adjustability of the bed. Gripping contact may be enhanced by a gripping surface at a support surface-contacting end of each leg. Adjustability for contact with the supporting surface, may be advantageously assisted by a side wall of each lower frame end being provided with an elongated, generally vertically aligned slot (not shown), in operative combination with a thumb screw (not shown), like operation of slot 541 and thumb screw 543 of FIG. 25.

Removal of the wheel assemblies also beneficially allows clamp assembly 54 to be removed from the apparatus in applications in which as indicated in FIGS. 17 and 18, the space requirements of the wheel assemblies would be of disadvantage, and/or obstructing or available structure precludes use of the clamp assembly and it is desired to remove the clamp assembly from the apparatus. To this end after removal of the wheel assemblies, the pivotably mounted lever of the ratchet clutch can be pivoted to an appropriate lever position for downward movement of the clamp assembly, and the clamp assembly is removed. Removability of the wheel assemblies may also be beneficial for shipment or storage.

When clamp assembly 54 has been removed or the elongated jaws of clamp assembly 54 are in the stow position, downwardly facing clamps 50 and side clamping assembly 52 remain for securing the apparatus to available support structure. Adjustability of clamps 50 along the x-axis (shown in FIG. 12) is advantageous for a headboard having sides that converge toward its top as illustrated in FIG. 18. Taking advantage of spaced apart, threaded apertures 78 of the frame members, side clamping assembly 52 may be beneficially attached to front frame lower ends 122, for maximized spacing distance between the downwardly facing, upper clamps and the lower clamps. With continued reference to FIG. 17, if there is sufficient clearance, clamp assembly 54 with the elongated jaws in the stow position, could have been positioned above side clamps 52.

Referring to an apparatus 410 of FIGS. 19 and 20, the various clamps and the wheel assemblies may be dispensed with altogether. Apparatus 410 includes a support frame formed like that of apparatus 10 by a pair of spaced apart, generally parallel, frame members 12 connected by spaced apart crossbars 14, and in addition a wall-mounted frame 411. Like apparatus 10, each frame member is advantageously provided along its length with a plurality of suitably spaced threaded apertures 78. With threaded thumb screws 104, a protective housing 212 for the power springs, pull-line wheels and associated structure (not shown), is mounted on the support frame, and apertures 78 provide for vertical adjustment of the mounting position.

Similarly, the wall-mounted frame is beneficially provided along its length with a plurality of suitably spaced apart, threaded apertures 413 for mounting of the support frame and adjustment of the vertical mounting position of the support frame. Threaded mounting bolts 415 extend through suitably spaced apart apertures 417 conveniently in the crossbars, and into apertures 413. Use of the crossbars for mounting the support frame to the wall-mounted frame conveniently allows all of apertures 78 to be available for vertical adjustment of the housing mounting position. Conveniently, to provide for attachment of the support frame to the wall-mounted frame using crossbar apertures 417, support frame members 12 are spaced apart a greater distance than frame members 419 of the wall-mounted frame are spaced apart.

Conveniently, housing 212 is attached to front walls 74 of the support frame, instead of to the rear walls as in the case of apparatus 10. As can readily be recognized, this location of the pull-line wheels simplifies feed of pull-lines 28 from the housing to advantageously angularly positionable, guide wheels 24, and the housing exit locations (defined by the locations of bearings 366) of the pull-lines may now be conveniently aligned as indicated in FIG. 20, with a back of a respective grooved rim 26 of respective guide wheel 24. A protective cover (not shown) can be used to cover guide wheels 24.

Beneficially, for carrying the support frame and associated structure of apparatus 410, apparatus 410 is provided with one or more carry handles 421. As shown, the carry handles may conveniently be attached to housing 212. For the sake of brevity in the description of apparatus 410, the previously used numbering has been used with like features for the like or same parts, it being understood that reference can be made to the earlier description; and the description has been primarily limited to different features.

If desired, carry handles may be provided for apparatus 10 and the previously described extensible legs may be used in place of wheel assemblies 378. However, as will be readily appreciated, a wheeled base is of considerable benefit for moving an apparatus in accordance with the invention, and may be advantageous for supporting contact of the apparatus with a supporting surface. In this respect, it will be recognized that an apparatus in accordance with the present invention, may include other suitable wheeled bases, and furthermore that such wheeled bases may remain in supporting contact with a supporting surface and provide support after the apparatus has been secured to suitable support structure, and include the wheeled base described in U.S. Pat. No. 5,005,829 and shown in FIG. 2 thereof. It will also be understood that the support frame may be generally perpendicular to the wheeled base, as shown in that patent.

Because of the varied means of securing an apparatus in accordance with the invention, to support structure, and because an apparatus in accordance with the invention may utilize a variety of supporting bases, the support structure need not include a headboard or footboard. Rather, the support structure need only be sufficient that an apparatus in accordance with the invention, can be secured into position.

With reference now to FIGS. 21–27, apparatus in accordance with the present invention, may be used to exert a desired pulling force, and maintain the pulling force. Referring particularly to FIGS. 21–25, an apparatus 510 may be used to assist in spinal alignment as indicated. With reference to FIG. 24 in particular, apparatus 510 conveniently includes a left handed spring/wheel (CW-winding pull-line wheel 282 indicated; CCW-winding power spring not shown). It will be readily recognized that a right handed spring/wheel could be used instead by, for instance, relocating pull-line wheel 282 and the associated structure to an otherwise unused, left half of housing 212. Especially differentiating apparatus 510 from apparatus 10 is a generally L-shaped guide member 525. Beneficially, a housing exit bearing 366, a directing wheel 368, a guide wheel 24, and guide member 525 are generally centrally located between frame members 12.

Figure 25:
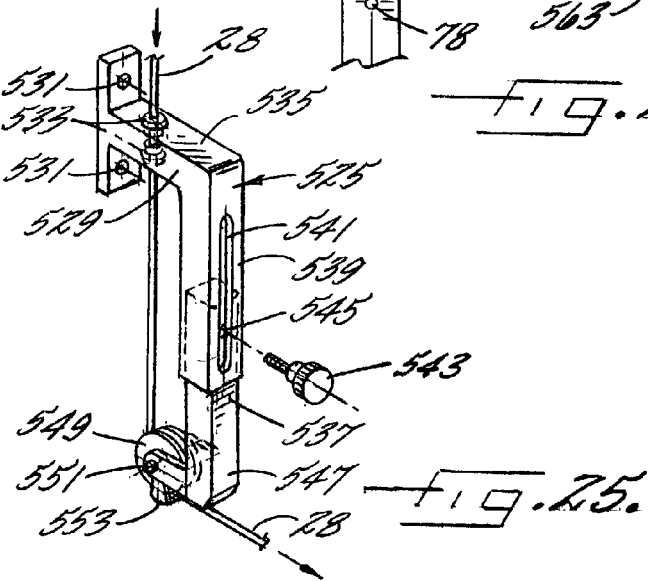
FIG. 25 is a perspective view showing further details of the guide member of the apparatus of FIG. 21.

Referring now particularly to FIGS. 21 and 25, guide member 525 is conveniently attached to the support frame by a positioning plate 526 that, like adjustment plate 72 for clamps 50, conveniently extends from over a front wall 74 of one frame member to over a front wall 74 of the other frame member, and includes threaded apertures (not shown) for receiving threaded thumb screws 528. Vertical adjustability of plate 526 and guide member 525 is provided by a plurality of spaced apart apertures (not shown) in the frame members, as previously described for clamps 50 of apparatus 10. Similarly, as shown in FIG. 21, a pulley block 372 of directing wheel 368 is attached to rear walls 100 of the support frame by a positioning plate 527 like plate 526.

A T-shaped upper end 529 of guide member 525 includes mounting apertures 531 through which the thumb screws extend into support plate 526, and in addition, includes spaced apart bearings 533 in a generally horizontally extending arm portion 535 through which pull-line 28 passes from guide wheel 24. Adjustability of the vertical extent of the guide member is conveniently provided by an extensible end 537 that is slidably held within a downwardly extending, generally vertically oriented, sleeve-like leg 539 provided with an elongated, generally vertically aligned slot 541 (best seen in FIG. 25) through which a thumb screw 543 extends into a threaded bore 545 in extensible end 537 of the guide member. Rotatably mounted to a lower end 547 of the extensible end is a second guide wheel 549, which is mounted on an axle 551, which also supports a U-shaped, pull-line support member 553. As illustrated, the pull-line conveniently extends downwardly from the guide wheel through bearings 533, and then passes between the second guide wheel and the U-shaped support member.

In use, apparatus 510 is secured to appropriate support structure (indicated in FIG. 21 in phantom) beneficially by upper clamps 50, side clamping assembly 52 and clamp assembly 54. As previously indicated, the use of apparatus 510 need not be limited to a hospital bed. Furthermore, as may be understood from FIGS. 19 and 20, the support frame may be attached to a wall, in which case housing 212 may be attached to front walls 74 of the frame members and arm portion 535 may be provided with an additional pair of spaced apart bearings through which the pull-line passes from housing 212 to guide wheel 24.

In any event, the vertical extent of the guide member is beneficially adjusted so that the elevation of guide wheel 549 and hence of the pull-line may be adjusted. In this way, the pulling force exerted on a head-attachment structure 555 or the like can be selected to be at a medically appropriate angle. For spinal alignment, an appropriate angle may be as illustrated by FIG. 21, such that between the guide member and the reclining patient's head (shown in phantom), the pull-line and head-attachment structure are linear and generally parallel to the horizontal plane defined by the patient's bed (also shown in phantom). A swivel bearing 557 is advantageously connected to the head attachment structure and disposed between the head attachment structure and pull-line end 30.

Figure 23:
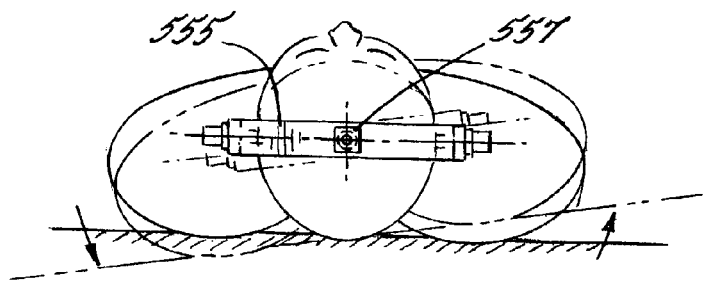
FIG. 23 is an end view taken substantially along a line 23—23 of FIG. 21, illustrating pivotable motion of the head attachment structure about a pivot point, consistent with the illustrated change in the relative orientation of the patient's body.

After adjustment of the vertical extent of the guide member and the pull-line end is secured to the head attachment structure, a spring-biased, locking pin 234 is retracted from its locking pin-receiving aperture 238 (only aperture 238 in the 6 o'clock position can be seen in FIGS. 21 and 24) and an axle crank 200 is rotated CCW and the power spring is wound CCW until an appropriate pulling force is applied to the head-attachment structure by the force exerted by the power spring on pull-line wheel 282 (indicated in FIG. 24). When an appropriate pulling force is obtained, the locking pin is released into an appropriate locking pin-receiving aperture (indicated to be at the 12 o'clock position in FIG. 24). To provide assurance that the pulling force is not inadvertently reduced, conveniently a thumb screw 561 or like securing member may be threaded into a threaded aperture 563 (shown in FIGS. 21 and 24) located adjacent and CW relative to the locking pin-receiving aperture to prevent CW rotation of the axle. If desired, the damping assembly (indicated by adjustment bolt 306) may be used to apply sufficient frictional pressure to the pull-line wheel rim to overcome the force exerted by the power spring on the pull-line wheel; however, this choice may be disadvantageous as it would prevent power spring tension from causing the pull-line wheel to rotate CCW to take up any pull-line slack. As illustrated in FIG. 23, swivel bearing 557 or the like assists pivotable movement of the head attachment structure as a patient is changed in elevation on a bed from side to side, so that a constant pulling force is maintained on the patient's head.

As will be readily recognized, guide wheel 24 does not need to be angularly positionable in this application. Thus, pulley block 22 for the guide wheel may be non-pivotably attached to the support frame. The inertia disc may be omitted if desired or appropriate. For the sake of brevity in the description of apparatus 510, the previously used numbering has been used with like features for the like or same parts, it being understood that reference can be made to the earlier description. Thus, the description has been primarily limited to different features.

Figure 26:
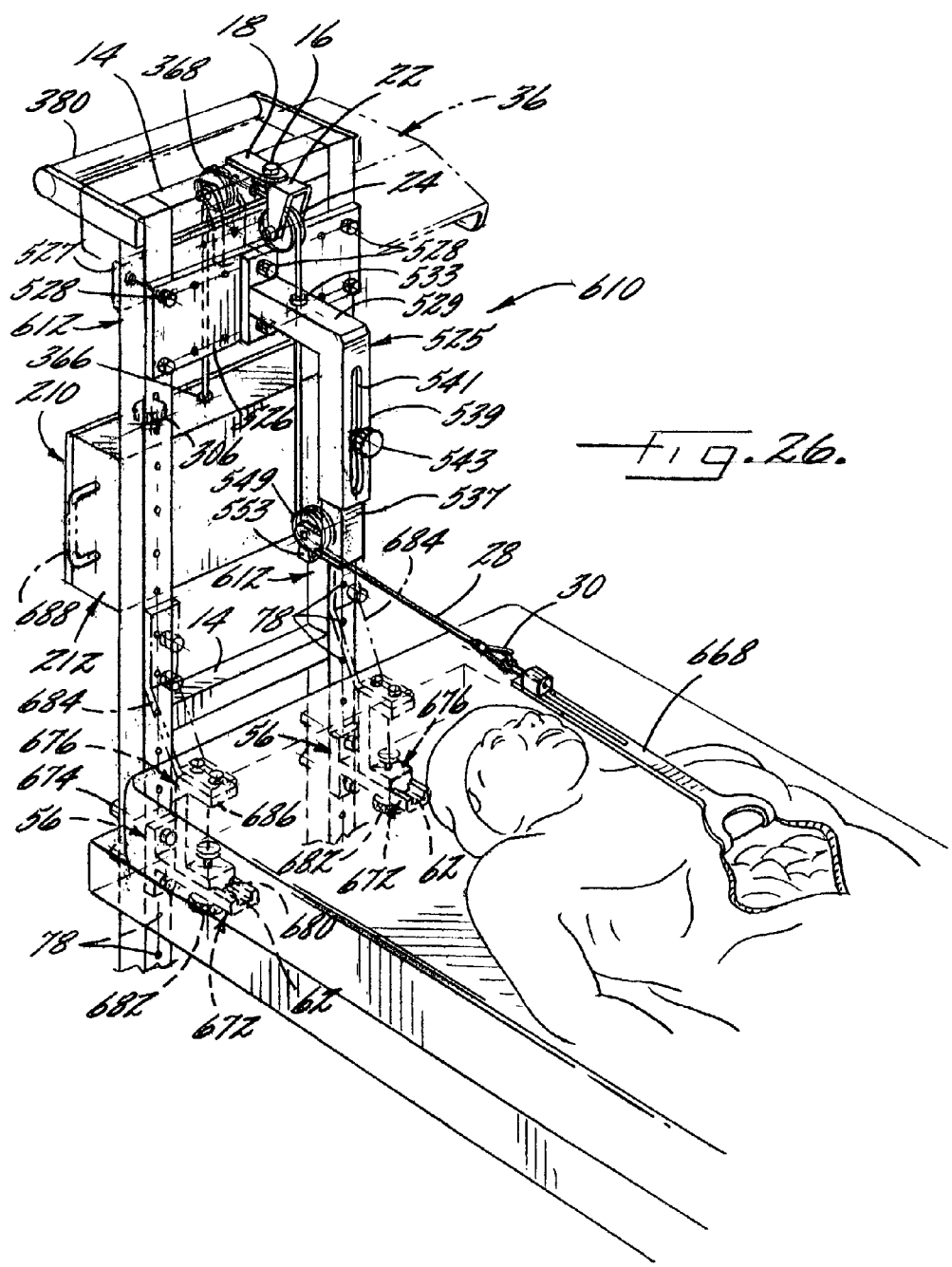
FIG. 26 is a perspective view of a fourth preferred embodiment in accordance with the present invention, conveniently mounted to a surgical table and exerting a pulling force on a surgical retractor, and in phantom line, showing a carry handle, support brackets, and protective cover.
Figure 27:
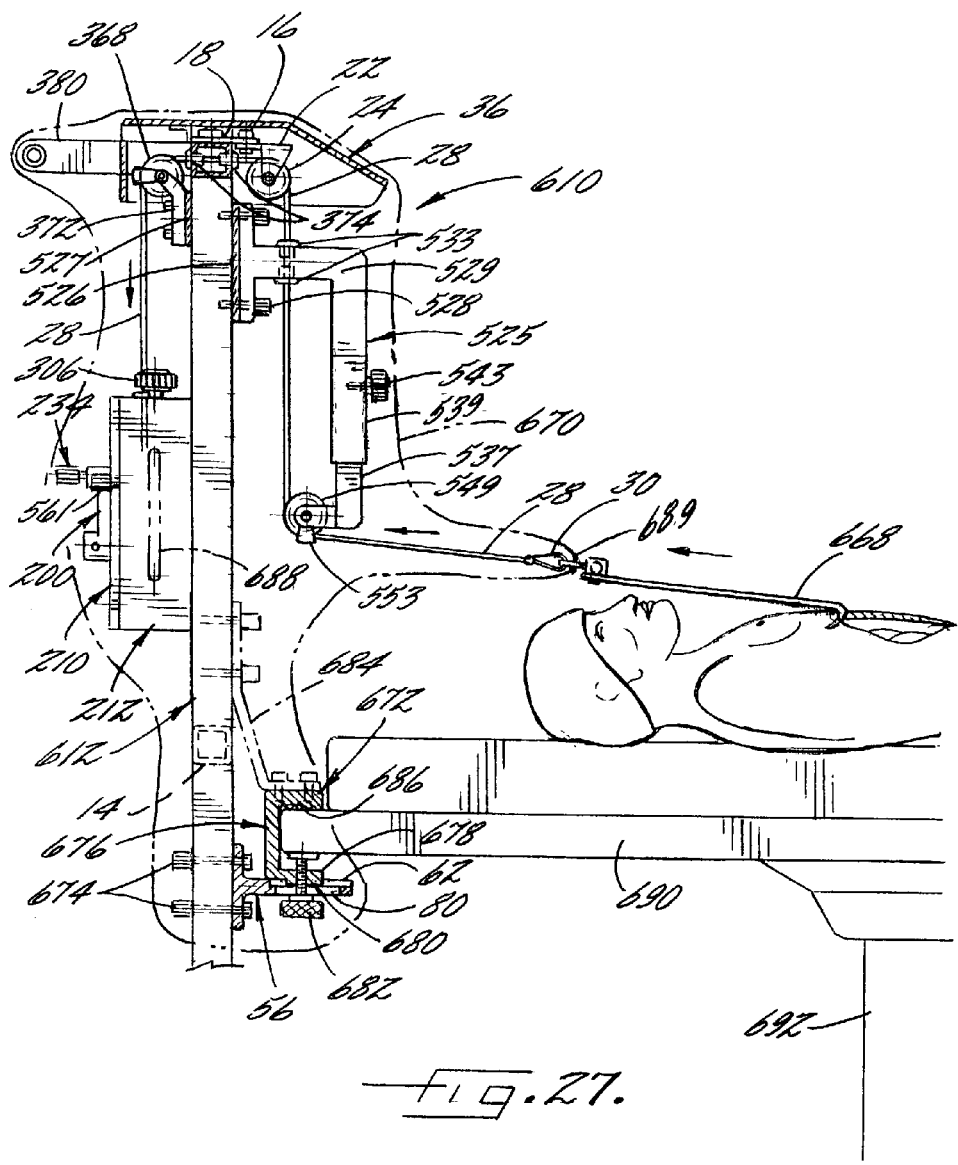
FIG. 27 is a side view of the apparatus and its use illustrated in FIG. 26, and in phantom line also illustrating a sterile shroud.

With reference now to FIGS. 26 and 27, an apparatus 610 in accordance with the invention, may be used to exert a pulling force on a retractor or the like used in surgical operations. Retractors are used to provide skin or tissue retraction and expose internal body organs or the like. In accordance with the invention, a pull-line end 30 of apparatus 610 is secured to a retractor 668 or the like, and a desired pulling force is applied to the retractor beneficially using an adjustable guide member 525, and thereafter maintained, as previously described.

For the sake of brevity in the description of apparatus 610, the previously used numbering has been used with like features for the like or same parts, it being understood that reference can be made to the earlier description. Thus, the description of apparatus 610 is primarily limited to features different from those of apparatus 510.

As indicated in FIGS. 26 and 27, frame members 612 may extend to a base that remains on the floor or a like surface and supports the apparatus after the apparatus has been secured to suitable support structure, as previously described. Otherwise, frame members 612 may, as indicated by the location of the broken lines in FIGS. 26 and 27, conveniently terminate below and proximate to a pair of spaced apart, clamping assemblies 672.

U-shaped clamps 672 conveniently secure apparatus 610 to an operating table 690 mounted on a pedestal 692. The U-shaped clamps each include a slotted, generally T-shaped bracket 56 mounted to the respective frame member by bolts 674, which extend through apertures 78. Clamps 672 each further include a U-shaped member 676 that includes a lower arm 678 provided with a downwardly extending portion 680 (see FIG. 27) of relatively reduced size to snugly slide within a guide channel 62 of T-shaped bracket 56 for forward/rearward adjustment of the U-shaped member. A clamp bolt 682 extends through a bore in lower arm 678 of each U-shaped member. After forward/rearward positioning of the U-shaped members, the clamp bolts are tightened into place.

If desired, for instance when frame members 612 do not extend to a supporting base, apparatus 610 may conveniently include braces 684 and a carry handle 688, shown in phantom. The braces are advantageously provided with slotted adjustment holes (not shown), and are each conveniently bolted using the adjustment holes to the respective frame member and an upper arm 686 of the respective U-shaped member.

Beneficially in accordance with the invention, an extensible end 537 of guide member 525 may be extended or retracted to define or change the angle of the pulling force, for instance, to provide an appropriate upward angle that lifts outer body tissue and allows greater access to inner body parts. With reference to FIG. 27, to maintain a sterile operating field in a surgical environment, a sterile shroud 670 may envelop or cover apparatus 610. Advantageously, shroud 670 includes an access port 689 through which an end of the surgical retractor extends for connection with the pull-line.

If desired, guide wheel 549 may be mounted to extensible end 537 of guide member 525 so as to be angularly positionable. An additional pull-line and associated apparatus including an additional guide member, may be used.

From time to time, it may be necessary to secure apparatus 10 to support structure that of itself may tend to have some movement from its normal position. For example, a headboard could have a tendency to move some from a normally true vertical position toward or away from a bed. Beneficially, in such a case, when the apparatus has been secured to the support structure and in particular clamp assembly 54 has been engaged with bed frame or head board frame support structure as illustrated in FIG. 7, the engagement of clamp assembly 54 would oppose any movement of such a headboard toward the bed. Furthermore, the smooth, steady retraction beneficially provided by the inertia disc and damping assembly, would prevent kinetic energy in the direction of such a headboard from producing motion of the headboard away from the bed. Furthermore, it will be understood that any such wobble can be reduced or eliminated by use of the previously described extensible legs or other suitable supporting surface-contacting bases. Also, a skilled artisan will readily recognize that useful conventional means include clamping or otherwise securing a headboard to a support frame, or using sleeves to reduce mechanical clearance between upwardly projecting headboard mounting pins and mounting pin-receiving bores of the headboard.

Various modifications may be made to an apparatus in accordance with the present invention, some of which have been described. It is therefore apparent that the present invention may be carried out with various modifications without departing from the spirit or essential attributes thereof. Accordingly, reference should be made to the appended claims as indicating the scope of the invention.

The invention claimed is:

1. A versatile health care apparatus comprising a pull-line; and a rotatable pull-line wheel mounted on an axle and operatively connected to a power spring for the exertion of torsional force on said pull-line wheel, wherein said pull-line has an end in connection with said pull-line wheel and said power spring is in connection with said axle;
   further comprising a load-adjusting, axle rotating member where upon rotating said in an appropriate rotational direction, restraint of rotation of said pull-line wheel in the like rotational direction applies energy to said power spring;
   an axle rotation-preventing member that is disengaged during axle rotation, but otherwise is in an axle rotation-preventing engaged position, and
   a wall through which an end of said axle extends wherein said wall is provided with a plurality of apertures for receiving an end of said axle rotation-preventing member.

2. The apparatus of claim 1, further comprising a pulley block and a guide wheel for an opposite end of said pull-line, wherein said opposite end of said pull-line is restrained from being retracted through a throat formed by said pulley block and said guide wheel, to thereby effect said restraint of rotation of said pull-line wheel.

3. The apparatus of claim 1, further comprising a rotatably mounted load-indicator wheel driven by rotation of said axle by said axle rotating member, wherein said axle rotating member is manually operable and mounted on said axle and comprises a bore through which said axle rotation-preventing member extends, and wherein said wall is provided with an aperture for viewing load-indicating indicia on said load-indicator wheel.

4. The apparatus of claim 1, wherein said power spring is a flat coil spring mounted on said axle and an end of said power spring is fixed to said axle, and said pull-line wheel is connected by a connecting pin that extends from a face of said pull-line wheel, to an opposite end of said power spring.

5. A versatile health care apparatus comprising a pull-line; and a rotatable pull-line wheel mounted on an axle and operatively connected to a power spring for the exertion of torsional force on said pull-line wheel, wherein said pull-line has an end in connection with said pull-line wheel and said power spring is in connection with said axle;
   comprising a load-adjusting, axle rotating member wherein upon rotating said axle in an appropriate rotational direction, restraint of rotation of said pull-line wheel in the like rotational direction applies energy to said power spring,
   further comprising a spring-biased brake shoe in frictional contact with a rim of said pull-line wheel, and a threaded member for adjustment of the spring-biased frictional contact.

6. The apparatus of claim 5, further comprising an inertia disc mounted on said axle and in connection with a face of said pull-line wheel for rotation with said pull-line wheel, wherein said inertia disc comprises an aperture through which a connecting pin extends for the connection of said pull-line wheel to said power spring.

7. The apparatus of claim 5, wherein said axle rotating member is mounted on said axle and is manually operable, further comprising a rotatably mounted load-indicator wheel driven by rotation of said axle by said axle rotating member, and a wall through which an end of said axle extends wherein said wall is provided with an aperture for viewing load-indicating indicia on said load-indicator wheel.

8. A versatile health care apparatus comprising a pull-line; and a rotatable pull-line wheel mounted on an axle and operatively connected to a power spring for the exertion of torsional force on said pull-line wheel, wherein said pull-line has an end in connection with said pull-line wheel and said power spring is in connection with said axle; and wherein upon connecting an opposite end of said pull-line with a medically useful device and rotating said axle in an appropriate rotational direction, a selected pulling force is exerted by said medically useful device on a patient's body, by the torsion exerted by said power spring on said pull-line wheel; further comprising an extendible guide member and an associated elevation adjustable guide wheel for said pull-line, for adjusting the angle of the pulling force.

9. The apparatus of claim 8, further comprising a force-adjusting, axle rotating member, and a locking pin for maintaining said selected pulling force, wherein said guide member is slidably extendible.

10. The apparatus of claim 8, wherein said medically useful device is useful for traction.

11. A versatile health care apparatus comprising a pull-line; and a rotatable pull-line wheel mounted on an axle and operatively connected to a power spring for the exertion of torsional force on said pull-line wheel, wherein said pull-line has an end in connection with said pull-line wheel and said power spring is in connection with said axle;
   comprising a force-adjusting, axle rotating member wherein upon connecting an opposite end of said pull-line with a medically useful device and rotating said axle in an appropriate rotational direction, a selected pulling force is exerted by said medically useful device on a patient's body, by the torsion exerted by said power spring on said pull-line wheel;
   an axle rotation-preventing member that is disengaged during said axle rotation, and
   a wall through which an end of said axle extends wherein said wall is provided with a plurality of apertures for receiving an end of said axle rotation-preventing member to maintain said selected pulling force.

12. The apparatus of claim 11, further comprising an indicator of the amount of said pulling force applied to the patient's body, said indicator comprising a rotatably mounted wheel driven by said axle rotation, and wherein said axle rotation-preventing member is spring-biased.

13. The apparatus of claim 11, wherein said medically useful device is a head-attachment structure useful for traction.

14. The apparatus of claim 13, wherein said head attachment structure is adapted for pivotable movement about a pivot point.

15. A versatile health care apparatus comprising a pull-line; and a rotatable pull-line wheel mounted on an axle and operatively connected to a power spring for the exertion of torsional force on said pull-line wheel, wherein said pull-line has an end in connection with said pull-line wheel and said power spring is in connection with said axle; and wherein upon connecting an opposite end of said pull-line with a medically useful device and rotating said axle in an appropriate rotational direction, a selected pulling force is exerted by said medically useful device on a patient's body, by the torsion exerted by said power spring on said pull-line wheel; further comprising a sterile shroud for said versatile health care apparatus.

16. The apparatus of claim 15, further comprising a force-adjusting, axle rotating member; a locking pin for maintaining said selected pulling force; a rotatably mounted load-indicator wheel driven by rotation of said axle by said axle rotating member; and a wall through which an end of said axle extends wherein said wall is provided with a plurality of apertures for receiving an end of said locking pin, and with an aperture for viewing load-indicating indicia on said load-indicator wheel.

17. The apparatus of claim 15, wherein said medically useful device is for assisting in accessibility to an internal body part.

18. The apparatus of claim 15, wherein said sterile shroud comprises an access port for connection of said opposite pull-line end to said medically useful device.

19. A versatile health care apparatus comprising a support frame for a power spring, a pull-line connected to said power spring, and mounting apparatus for securing said support frame to varied support structures, wherein said mounting apparatus comprises at least one downwardly facing clamp adjustable with respect to a z-axis, and at least one cooperating clamp connected to a rack and pinion mechanism for driving said cooperating clamp with respect to a y-axis, and a lever-operated, y-axis direction control mechanism operably connected to said rack and pinion mechanism, for preventing movement of said cooperating clamp in at least one selected y-axis direction, said lever being pivotably mounted.

20. The apparatus of claim 19, wherein said cooperating clamp is upwardly angled during engagement with said support structure, and wherein at least one rack attached to said support frame, and a pinion gear in engagement with said rack and mounted on an axle supported by a bracket to which said cooperating clamp is pivotably connected, provide said rack and pinion mechanism.

21. The apparatus of claim 19, further comprising a second power spring and a pair of guide wheels supported by said support frame, and a second pull-line connected to said second power spring, wherein said guide wheels are ergonomically spaced apart a distance that benefits use of said pull-lines together.

22. A versatile health care apparatus comprising a support frame for a power spring, a pull-line connected to said power spring, and mounting apparatus for securing said support frame to varied support structures, wherein said mounting apparatus comprises at least one downwardly facing clamp adjustable with respect to a z-axis, and at least one cooperating clamp, wherein said cooperating clamp is mounted on a pivotably mounted shaft supported by a pair of spaced apart brackets, and a control pin that extends from a control member mounted on said shaft into an aperture provided in one of said brackets controls pivotable movement of said cooperating clamp to an upwardly angled position.

23. A versatile health care apparatus comprising a support frame for a power spring, a pull-line connected to said power spring, and mounting apparatus for securing said support frame to varied support structures, wherein said mounting apparatus comprises at least one downwardly facing clamp adjustable with respect to a z-axis, and at least one cooperating clamp adjustably mounted with respect to a y-axis, wherein said cooperating clamp is slidably mounted with respect to an x-axis when not engaged with said support structure.

24. A versatile health care apparatus comprising a support frame for a power spring, a pull-line connected to said power spring, and mounting apparatus for securing said support frame to varied support structures, wherein said mounting apparatus comprises at least one downwardly facing clamp adjustable with respect to a z-axis, and at least one cooperating clamp adjustably mounted with respect to a y-axis, wherein said mounting apparatus further comprises a side clamping assembly comprising a plurality of telescoping arms for adjustability with respect to an x-axis.

25. A versatile health care apparatus comprising a support frame for a power spring, a pull-line connected to said power spring, and mounting apparatus for securing said support frame to varied support structures, wherein said mounting apparatus comprises at least one downwardly facing clamp adjustable with respect to a z-axis, and at least one cooperating clamp adjustably mounted with respect to a y-axis, further comprising a housing for said power spring, wherein said downwardly facing clamp is adjustably secured with respect to said y-axis to a first face of said support frame, and said housing is adjustably secured with respect to said y-axis to a second and opposite face of said support frame.

* * * * *

UNITED STATES PATENT AND TRADEMARK OFFICE
CERTIFICATE OF CORRECTION

PATENT NO. : 7,060,013 B2 Page 1 of 1
APPLICATION NO. : 10/183474
DATED : June 13, 2006
INVENTOR(S) : John M. Steinbach, Kevin F. Bulson and Elbert D. Turner, III It is certified that error appears in the above-identified patent and that said Letters Patent is hereby corrected as shown below:

Claim 1, column 19,
Line 12, "where" should read "wherein", and after "said", insert --axle--.

Signed and Sealed this

Twentieth Day of April, 2010

David J. Kappos
*Director of the United States Patent and Trademark Office*